(12) United States Patent
Zhou et al.

(10) Patent No.: US 7,052,674 B2
(45) Date of Patent: May 30, 2006

(54) PROKINETICIN POLYPEPTIDES, RELATED COMPOSITIONS AND METHODS

(75) Inventors: Qun-Yong Zhou, Irvine, CA (US); Frederick J. Ehlert, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 10/323,157

(22) Filed: Dec. 18, 2002

(65) Prior Publication Data

US 2003/0113867 A1    Jun. 19, 2003

Related U.S. Application Data

(63) Continuation of application No. 10/016,481, filed on Nov. 1, 2001, now abandoned.

(60) Provisional application No. 60/245,882, filed on Nov. 3, 2000, now abandoned.

(51) Int. Cl.
| A61K 49/00 | (2006.01) |
| C12Q 1/00  | (2006.01) |
| G01N 33/53 | (2006.01) |
| C12N 9/00  | (2006.01) |

(52) U.S. Cl. .......................... 424/9.1; 435/4; 435/7.21; 435/183

(58) Field of Classification Search ................ 530/300; 435/6, 7.1, 69.1, 4, 7.21, 183; 514/2; 424/9.1
See application file for complete search history.

(56) References Cited

U.S. PATENT DOCUMENTS 6,485,938 B1 * 11/2002 Sheppard et al. .......... 435/69.1

FOREIGN PATENT DOCUMENTS

| EP | 1207198 | 5/2002 |
| GB | 2368065 | 4/2002 |
| WO | WO 98/46620 | 10/1998 |
| WO | WO 99/24055 | 5/1999 |
| WO | WO 99/63088 | 12/1999 |
| WO | WO 00/34334 | 6/2000 |
| WO | WO 00/52022 | 9/2000 |
| WO | WO 00/53753 | 9/2000 |
| WO | WO 00/70049 | 11/2000 |
| WO | WO 00/73454 | 12/2000 |
| WO | WO 00/75327 | 12/2000 |
| WO | WO 01/16309 | 3/2001 |
| WO | WO 01/36465 | 5/2001 |
| WO | WO 01/36471 | 5/2001 |
| WO | WO 01/40466 | 6/2001 |
| WO | WO 01/42288 | 6/2001 |
| WO | WO 01/48015 | 7/2001 |
| WO | WO 01/48188 | 7/2001 |
| WO | WO 01/53308 | 7/2001 |
| WO | WO 01/57190 | 8/2001 |
| WO | WO 01/57273 | 8/2001 |
| WO | WO 01/68699 | 9/2001 |
| WO | WO 01/68700 | 9/2001 |
| WO | WO 02/00690 | 1/2002 |
| WO | WO 02/00711 | 1/2002 |
| WO | WO 02/06483 | 1/2002 |
| WO | WO 02/08284 | 1/2002 |
| WO | WO 02/08288 | 1/2002 |
| WO | WO 02/08417 | 1/2002 |
| WO | WO 02/10387 | 2/2002 |
| WO | WO 02/16607 | 2/2002 |
| WO | WO 02/057443 | 7/2002 |
| WO | WO 02/061087 | 8/2002 |
| WO | WO 02/062944 | 8/2002 |
| WO | WO 02/064789 | 8/2002 |

OTHER PUBLICATIONS

Achem and Robinson, "A Prokinetic Approach to Treatment of Gastroesophageal Reflux Disease," *Dig. Dis.* 16:38-46 (1998).

Aravind et al., "A Colipase Fold in the Carboxy-Terminal Domain of the Wnt Antagonists—the Dickkopfs," *Curr. Biol.* 8:R477-478 (1998).

Boisbouvier et al., "A Structural Homologue of Colipase in Black Mamba Venom Revealed by NMR Floating Disulphide Bridge Analysis," *J, Mol. Biol.* 283:205-219 (1998).

Briejer et al., "Idiopathic Constipation: too few stools and too little knowledge", *Trends Pharmacol. Sci.* 20:1-3 (1999).

Cunningham et al., "Actin-Binding Protein Requirement for Cortical Stability and Efficient Locomotion," *Science* 255:325-327 (1992).

Eglen et al., "Muscarinic Receptor Subtypes and Smooth Muscle Function," *Pharmacol. Rev.* 48:531-565 (1996).

Fraker and Speck, "Protein and Cell Membrane Iodinations with a Sparingly Soluble Chloroamide, 1,3,4,6-TETRACHLORO-3a, 6a-diphenylglycoluril," *Biochem. Biophys. Res. Commun.* 80:849-857 (1978).

(Continued)

Primary Examiner—Janet L. Andres
Assistant Examiner—Gyan Chandra
(74) *Attorney, Agent, or Firm*—DLA Piper Rudnick Gray Cary US LLP

(57) ABSTRACT

The invention provides isolated polypeptides that stimulate gastrointestinal smooth muscle contraction, including human prokineticin 1 and human prokineticin 2 polypeptides, and functional fragments and modifications thereof. Also provided are methods of stimulating gastrointestinal smooth muscle contraction in a mammal, by administering to the mammal an effective amount of a prokineticin polypeptide. The invention also provides nucleic acid molecules encoding a prokineticin polypeptide, and antibodies that selectively bind a prokineticin polypeptide. Further provided are methods of identifying a prokineticin receptor ligand, agonist or antagonist.

3 Claims, 9 Drawing Sheets

OTHER PUBLICATIONS

Georgiou and Valax, "Expression of Correctly Folded Proteins in *Escherichia coli*", *Curr. Opin. Biotechnol.* 7:190-197 (1996).

Glinka et al., "Dickkopf-1 is a Member of a New Family of Secreted Proteins and Functions in Head Induction," *Nature* 391:357-362 (1998).

Li et al., "Modulation of Dopamine D2 Receptor Signaling by Actin-Binding Protein (ABP-280)," *Mol. Pharmacol,* 57:446-452 (2000).

Li et al., "Identification of two prokineticin cDNAs: recombinant proteins potently contract gastrointestinal smooth muscle,"*Mol. Pharmacol.* 59(4):692-698 (2001).

Li and McIver, "High-Accuracy Molecular Mass Determination for Peptides and Proteins by Fourier Transform Mass Spectrometry," *Anal. Chem.* 66:2077-2083 (1994).

Lilie et al., "Advances in Refolding of Proteins Produced in *E. coli,*" *Curr. Opin. Biotech.* 9:497-501 (1998).

Longo and Vernara, "Prokinetic Agents for Lower Gastrointestinal Motility Disorders," *Dis. Colon Rectum* 36:696-708 (1993).

Mollay et al., "Bv8, a Small Protein from Frog Skin and its Homologue from Snake Venom Induce Hyperalgesia in Rats," *Eur. J. Pharmacol.* 374:189-196 (1999).

Saito et al., "Molecular Characterization of the Melanin-Concentrating-Hormone Recepter," *Nature* 400:265-269 (1999).

Samsom and Smout, "Abnormal Gastric and Small Intestinal Motor Function in Diabetes mellitus," *Dig. Dis.* 15:263-274 (1998).

Sawyer and Ehlert, "Contractile Roles of the M2 and M3 Muscarinic Receptors in the Guinea Pig Colon," *J. Pharmacol. Exp. Ther.* 284:269-277 (1998).

Schweitz et al., "Purification and Pharmacological Characterization of Peptide Toxins from the Black Mamba (*Dendroaspis polylepis*) Venom," *Toxicon* 28(7):847-856 (1990).

Schweitz et al., "MIT1, a Black Mamba Toxin with a new and Highly Potent Activity on Intestinal Contraction," *FEBS Letters* 461:183-188 (1999).

Schweitz et al., "A New Member of the Natriuretic Peptide Family Is Present in the Venom of the Green Mamba (*Dendroaspis angusticeps*)," *J. Biol. Chem.* 267(20):13926-13932 (1992).

Thomas et al, "Functional Role for the $M_2$ Muscarinic Receptor in Smooth Muscle of Guinea Pig Ileum." *Mol. Pharma.* 44:102-110 (1993).

Tonini, "Recent Advances in the Pharmacology of Gastrointestinal Prokinetics," *Pharmacol. Res.* 33:217-226 (1996).

van Tilbeurgh et al., "Structure of the Pancreatic Lipase-Procolipase Complex," *Nature* 359:159-162 (1992).

von Heijne, "A New Method for Predicting Signal Sequence Cleavage Sites,"*Nucleic Acids Res.* 14:4683-4690 (1986).

Weschselberger et al., "The Mammalian Homologues of Frog Bv8 are Mainly Expressed in Spermatocytes," *FEBS* 462:177-181 (1999).

Jilek et al., "Murine Bv8 gene maps near a synteny breakpoint of mouse chromosome 6 and human 3p21," *Gene* 256:189-195 (2000).

Kaser et al., "The AVIT protein family," *EMBO Reports* 4(5):469-473 (2003).

* cited by examiner

A)          MRGATRVSIMLLLVTVSDC  AVITGA
B) MRSLCCAPLLLLLLLPPLLLTPRAGDA  AVITGA
C)          MKCFAQIVVLLLVIAFSHG  AVITGA
D)                               AVITGA

CERDVQCGAGTCCAISLWLRGLRMCTPLGREGEECHPG
CDKDSQCGGGMCCAVSIWVKSIRICTPMGKLGDSCHPL
CDKDVQCGSGTCCAASAWSRNIRFCIPLGNSGEDCHPA
CERDLQCGKGTCCAVSLWIKSVRVCTPVGTSGEDCHPA
 *      *  * *            *           *

SHKVPFFRKRKHHTCPCLPNLLCSRFPDGRYRCSMDLKNINF
TRKVPFFGRRMHHTCPCLPGLACLRTSFNRFICLAQK
SHKVPYDGKRLSSLCPCKSGLTCSK.SGEKFKCS
SHKIPFSGQRMHHTCPCAPNLACVQTSPKKFKCLSKS
 *  *        *            *

FIGURE 1

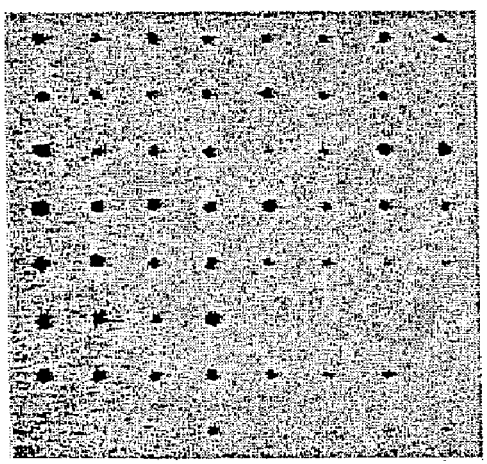
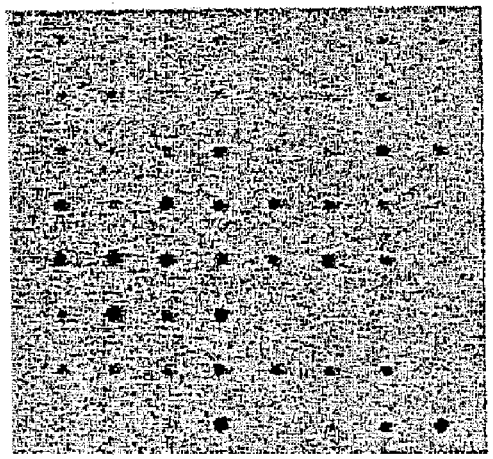
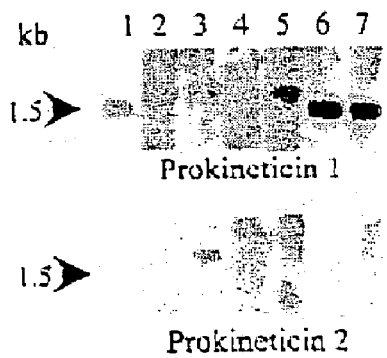
FIGURE 2

A
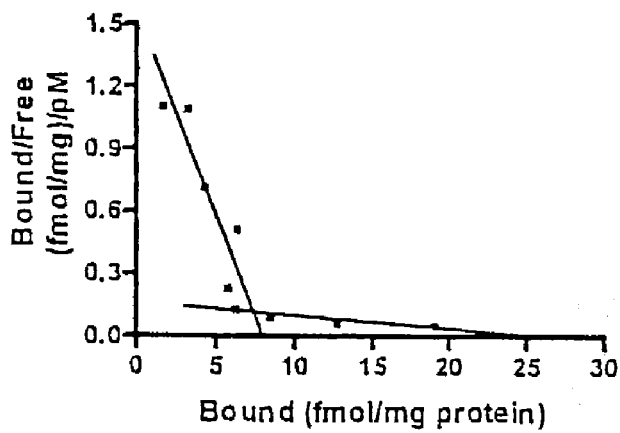
B
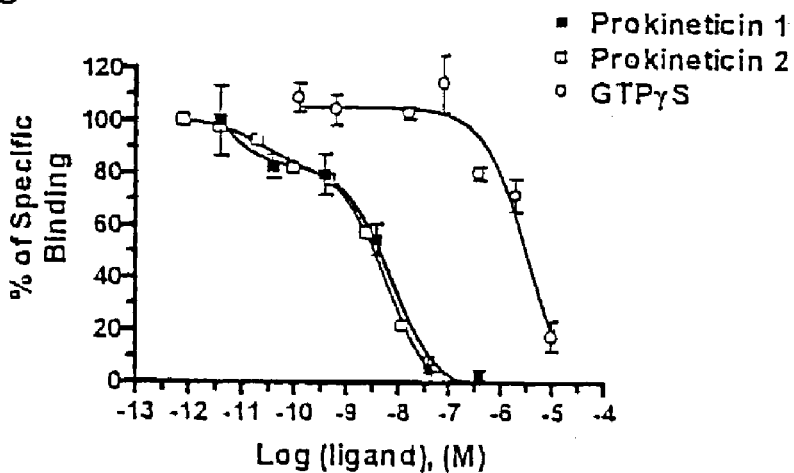
FIGURE 5

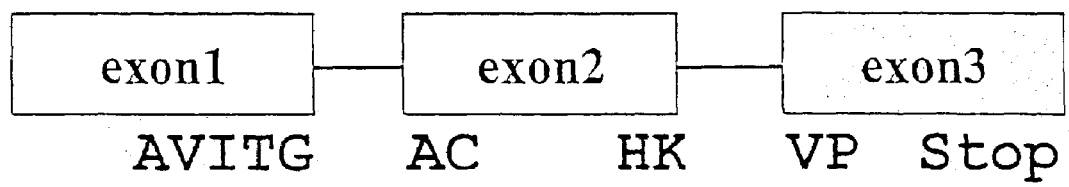
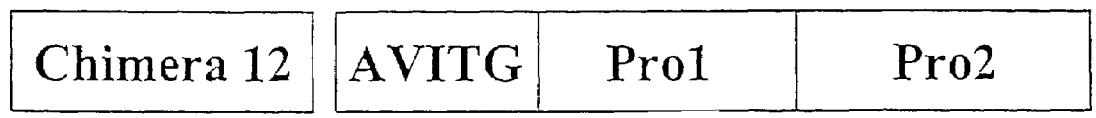
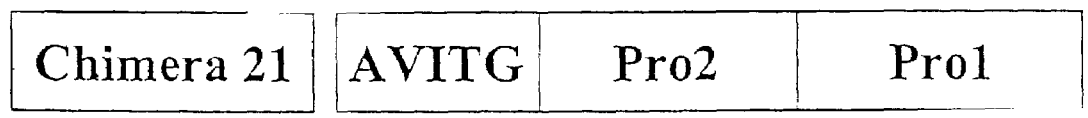
FIGURE 6

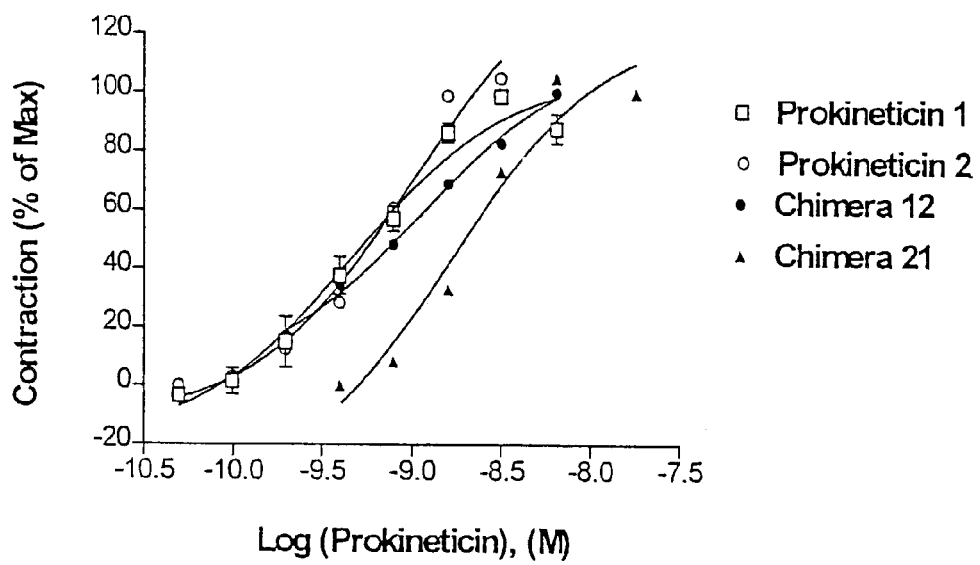
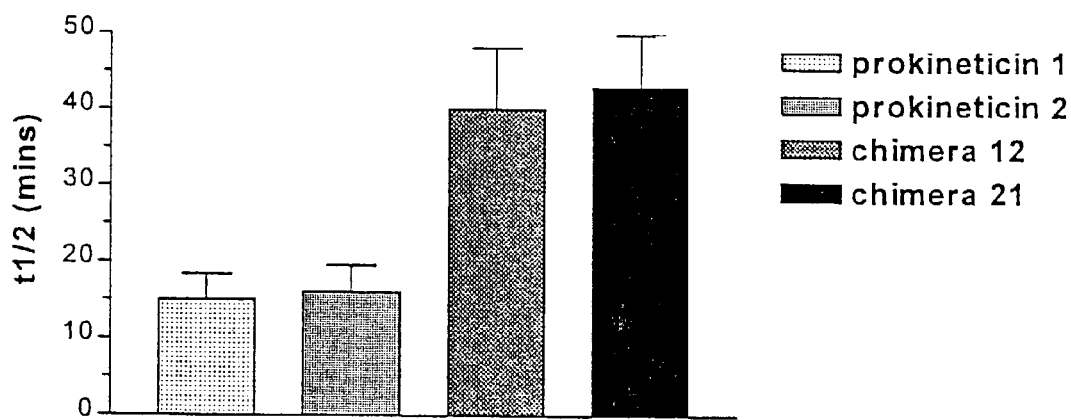
FIGURE 7

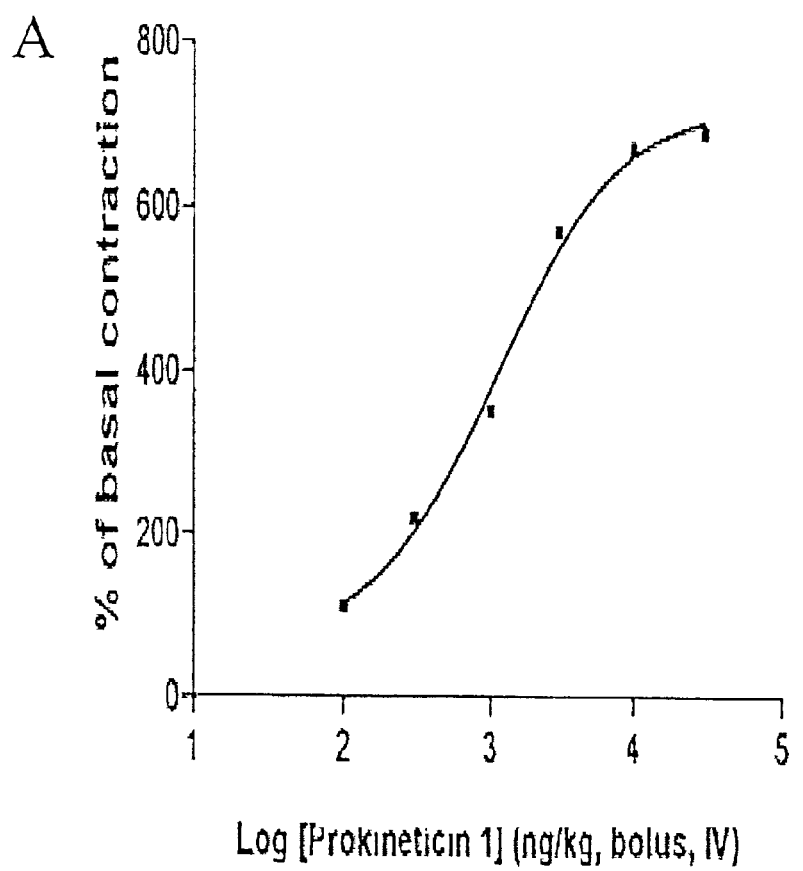
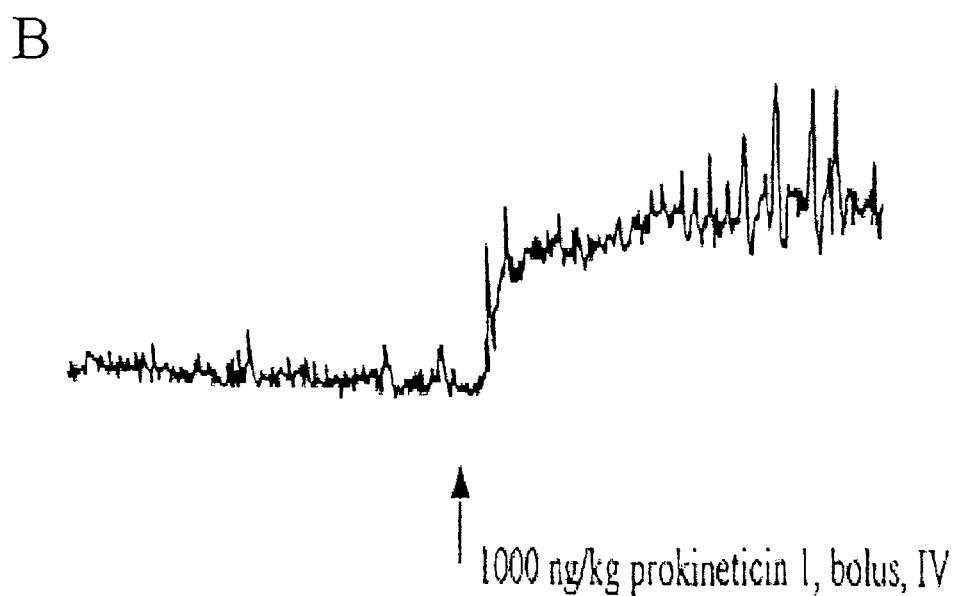
FIGURE 8

PROKINETICIN POLYPEPTIDES, RELATED COMPOSITIONS AND METHODS

This application is a continuation of application Ser. No. 10/016,481, filed Nov. 1, 2001, now abandoned which claims the benefit of U.S. Provisional Application Ser. No. 60/245,882, filed Nov. 3, 2000, now abandoned.

BACKGROUND OF THE INVENTION

The main function of gastrointestinal (GI) smooth muscle is to mix and propel intralumenal contents, which enables efficient digestion of food, progressive absorption of nutrients, and eventual evacuation of residual components. The activity of GI smooth muscle is regulated by intrinsic and extrinsic neural signals, including classical neurotransmitters, co-existing neuropeptides, and circulating peptide hormones. In addition, a number of humoral agents including histamine, serotonin, and adenosine that are produced by nonneural GI cells also influence the activity of smooth muscle cells.

A number of clinical conditions are associated with altered GI motility, including irritable bowel syndrome, diabetic gastroparesis, postoperational ileus, chronic constipation, gastrointestinal reflux disease, chronic diarrhea, infectious diseases, malabsorptive disorders, inflammatory bowel disorders, and intestinal cancers. The identification of regulators of gastrointestinal motility should facilitate the development of novel therapeutics for disorders that involve impaired or enhanced gastrointestinal motility.

Two potential regulators of gastrointestinal motility have recently been identified. Mamba intestinal toxin (MIT1), a small protein that potently stimulates the contraction of guinea-pig ileum, has been purified from mamba snake venom (Schweitz et al., *Toxicon* 28:847–856 (1990) and Schweitz et al., *FEBS Letters* 461:183–188 (1999)). Recently, a protein of similar size and having greater than 40% identity with MIT1, including all 10 conserved cysteines, has been purified from frog skin secretions (Mollay et al., *Eur. J. Pharmacol.* 374:189–196 (1999)). The frog protein, named Bv8, was also found to potently stimulate the contraction of GI smooth muscle.

Methods of recombinantly preparing these snake and frog polypeptides, or of recombinantly preparing other polypeptides containing 10 cysteines, have not previously been described, limiting the utility of these regulators for therapeutic use. Additionally, snake and frog polypeptides could elicit antibodies if administered to mammals that would likely reduce their efficacy as therapeutics.

Accordingly, there exists a need to identify endogenous human polypeptides that stimulate or inhibit gastrointestinal motility, and to develop methods of preparing these compounds recombinantly as therapeutics. There also exists a need to identify small molecule agonists and antagonists of endogenous gastrointestinal regulators that can be used therapeutically. The present invention satisfies this need, and provides related advantages as well.

SUMMARY OF THE INVENTION

The invention provides isolated polypeptides that stimulate gastrointestinal smooth muscle contraction. In one embodiment, the polypeptide contains an amino acid sequence at least 80% identical to the sequence of human prokineticin 1 (SEQ ID NO:3), wherein the sequence contains the N-terminal 6 amino acids of SEQ ID NO:3, the 10 conserved cysteine residues of SEQ ID NO:3, and from 0 to 9 of the 9 C-terminal amino acids of SEQ ID NO:3. In another embodiment, the polypeptide contains an amino acid sequence at least 80% identical to the sequence of human prokineticin 2 (SEQ ID NO:6), wherein the sequence contains the N-terminal 6 amino acids of SEQ ID NO:6, the 10 conserved cysteine residues of SEQ ID NO:6, and from 0 to 4 of the 4 C-terminal amino acids of SEQ ID NO:6.

Also provided are methods of stimulating gastrointestinal smooth muscle contraction in a mammal, by administering to the mammal an effective amount of a prokineticin polypeptide.

The invention also provides nucleic acid molecules encoding a prokineticin polypeptide.

Further provided are antibodies that selectively bind a prokineticin polypeptide.

The invention also provides methods of identifying a prokineticin receptor ligand, by contacting a preparation containing prokineticin receptor with one or more candidate compounds, and identifying a compound that specifically binds to the receptor. Such a compound is characterized as a prokineticin receptor ligand.

Also provided are methods of identifying a prokineticin receptor agonist, by contacting a preparation containing a prokineticin receptor with one or more candidate compounds, and identifying a compound that selectively promotes production of a prokineticin receptor signal. Such a compound is characterized as a prokineticin receptor agonist.

Further provided are methods of identifying a prokineticin receptor antagonist, by contacting a preparation containing a prokineticin receptor with one or more candidate compounds in the presence of a prokineticin, and identifying a compound that selectively inhibits production of a prokineticin receptor signal. Such a compound is characterized as a prokineticin receptor antagonist.

BRIEF DESCRIPTION OF THE DRAWINGS

FIG. 1 shows the amino acid sequences of A) prokineticin 1 precursor (SEQ ID NO:2); B) prokineticin 2 precursor (SEQ ID NO:4); C) frog BV8 (SEQ ID NO:11) and D) partial sequence of MIT 1 (SEQ ID NO:12). Ten conservative cysteine residues are marked (*). Signal peptides are underlined. The arrow indicates an intron splice site.

FIG. 2 shows the expression pattern of prokineticins. A human RNA master blot was probed with A) prokineticin 1 and B) prokineticin 2 cDNA. FIG. 2C show the blot diagram indicating the RNA sources for each dot. FIG. 2D shows a Northern blot analysis with prokineticin 1. Each lane contains RNA from different brain tissues as indicated: 1. Cerebellum; 2. Cerebral cortex; 3. Medulla; 4. Spinal cord; 5. Occipital pole; 6. Frontal lobe; 7. Temporal lobe; 8. Putamen; 9, Amygdala; 10. Caudate nucleus; 11. Corpus callosum; 12. Hippocampus; 13. Whole brain; 14. Substanti anigra.; 15. Subthalamic nucleus; 16. Thalamus.

FIG. 4D shows the concentration-response relationship for the contractile effects of prokineticins. Results are given as percentage of maximum contractility. Data are from three independent experiments. Contractile effects of oxotremorine-M in ileum in the absence (E) and in the presence of verapamil(1 μM; F) are also shown. Arrows indicate when drugs were added.

FIG. 5A shows Scatchard analysis of the specific binding of $^{125}$I-prokineticin 1 to guinea pig ileal membrane. FIG. 5B shows the inhibition of binding of $^{125}$I-prokineticin 1 (20 pM) by different concentrations of unlabeled prokineticin 1 (filled squares) and unlabeled prokineticin 2 (open squares). Open circles show displacement of $^{125}$I-prokineticin 1 (20 pM) with different concentrations of GTPγS.

FIG. 6 shows a schematic diagram of chimeras constructed between prokineticin 1 and prokineticin 2, designated chimera 12 (SEQ ID NO:13) and chimera 21 (SEQ ID NO:14).

FIG. 7 shows functional characterization of chimeric prokineticins. FIG. 7A shows a dose-response curve of chimeric and wild type prokineticins assayed for their ability to contract guinea-pig ileum. FIG. 7B shows time constants of chimeric and wild type prokineticins. The time constant indicates the time elapsed from peak contraction to midway contraction (half way from peak to sustained plateau contraction). After normalizing against the oxotremorine M-induced contraction, the peak and sustained plateau contraction elicited by prokineticins are about 80% and 40%, respectively. The midway contraction is thus about 60% of maximum contraction.

FIG. 8A shows the effect of administration of various doses of prokineticin 1 as an IV bolus on contractions in guinea pig ileum in vivo. FIG. 8B shows the contractile response to 1000 g/kg of prokineticin 1.

DETAILED DESCRIPTION OF THE INVENTION

Figure 3:
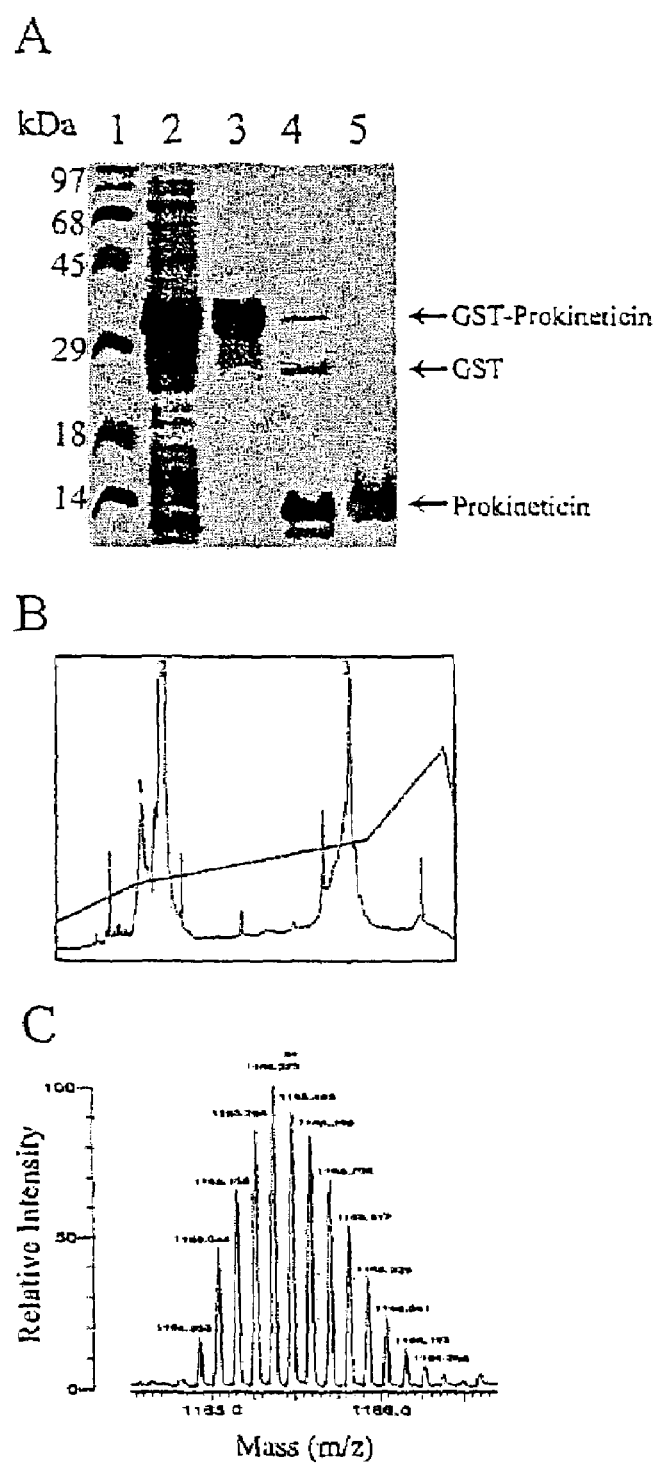
FIG. 3 shows the production and purification of human prokineticins: A) SDS-PAGE (18%) of prokineticin samples stained with Coomassie blue G-250. Lane 1, molecular weight standards; lane 2, whole bacterial lysate after induction; lane 3, Ni-NTA affinity chromatography-purified prokineticin; lane 4, Factor Xa digested prokineticin; lane 5, refolded prokineticin after HPLC purification. Each lane was loaded with 10–15 μg total protein. B) Reverse phase HPLC separation of refolded protein mixture. Peak 2 contains refolded prokineticin. C) Electrospray mass spectrum of refolded prokineticin 1.

The invention provides an isolated prokineticin polypeptide that is able to stimulate gastrointestinal (GI) smooth muscle contraction. The prokineticin polypeptides of the invention can be used, for example, in therapeutic methods to treat disorders involving impaired GI motility. Such polypeptides can also be used, for example, in screening methods to identify prokineticin receptor ligands, including receptor agonists and antagonists, which can be used therapeutically to treat disorders involving impaired or enhanced GI motility.

As used herein, the term "prokineticin polypeptide" refers to a polypeptide comprising the amino acid sequence of human prokineticin 1 shown as the non-underlined sequence in FIG. 1A (SEQ ID NO:3), or comprising the amino acid sequence of human prokineticin 2 shown as the non-underlined sequence in FIG. 1B (SEQ ID NO:6); and to a polypeptide containing minor modifications to SEQ ID NOS:3 or 6 that has GI smooth muscle contractile activity; and to a fragment of the reference polypeptide that has GI smooth muscle contractile activity.

As used herein, the terms "comprising," "having," "encoding," and "containing," and derivatives of these terms, are intended to be open-ended. The term "consisting" is intended to be closed-ended.

As used herein, the term "minor modification" to the sequences designated SEQ ID NOS:3 or 6 refers to one or more additions, deletions or substitutions compared with the recited amino acid sequence; one or more chemical or enzymatic modifications to the polypeptide; or substitution of one or more L-configuration amino acids with corresponding D-configuration amino acids. Such modifications can be advantageous, for example, in enhancing the stability, expression, bioactivity, or receptor affinity of the polypeptide, or for facilitating its identification or purification.

The GI smooth muscle contractile activity of a modified polypeptide can be determined by ex vivo or in vivo methods known in the art, such as the ex vivo and in vivo guinea pig ileal bioassays described in the Example, to confirm that it has GI smooth muscle contractile activity. Suitable assays for determining GI smooth muscle contractile activity can alternatively be performed using other GI smooth muscle tissue that responds to prokineticin 1 or 2, such as fundic muscle strip or proximal colon (see Example). Likewise, suitable assays can be performed using other mammals, including, for example, mice, rats, cats, dogs, sheep, goats, pigs, cows and primates.

A modified prokineticin polypeptide that elicits GI smooth muscle contractile activity can elicit at least 10%, 25%, 50%, 75%, 100% or more of the maximal GI smooth muscle contraction of human prokineticin 1 or 2, under the same conditions. A modified prokineticin polypeptide that elicits GI smooth muscle contractile activity can be less potent, similarly potent, or more potent than human prokineticin 1 or 2, under the same conditions. For example, a modified polypeptide can have an $EC_{50}$ that is 5-fold, 10-fold, 50-fold or 100-fold higher or lower than the $EC_{50}$ for human prokineticin 1 or 2. A modified prokineticin polypeptide that elicits GI smooth muscle contractile activity can also elicit contractions for the same duration or for a longer or shorter duration than human prokineticin 1 or 2, under the same conditions.

A chimeric polypeptide encoded by exons 1 and 2 of prokineticin 1 and exon 3 of prokineticin 2, designated chimera 12 (SEQ ID NO:13) (see FIG. 6) is an example of a modified prokineticin that elicits ileal contractions with a similar potency as prokineticins 1 or 2 (see FIG. 7A), but which causes prolonged contractions in comparison with prokineticins 1 or 2 (see FIG. 7B).

A chimeric polypeptide encoded by exons 1 and 2 of prokineticin 2, and exon 3 of prokineticin 1, designated chimera 21 (SEQ ID NO:13) (see FIG. 6) is an example of a modified prokineticin that elicits ileal contractions with an 8-fold lower potency than prokineticins 1 or 2 (see FIG. 7A), and which causes prolonged contractions in comparison with prokineticins 1 or 2 (see FIG. 7B).

Modifications to the amino acid sequence designated SEQ ID NOS:3 or 6 can be randomly generated, such as by random insertions, deletions or substitutions of nucleotides in a nucleic acid molecule encoding SEQ ID NOS:3 or 6. Alternatively, modifications can be directed, such as by site-directed mutagenesis of a nucleic acid molecule encoding SEQ ID NOS:3 or 6.

Computer programs known in the art can provide guidance in predicting which amino acid residues can be modified without abolishing the function of the polypeptide (see, for example, Eroshkin et al., *Comput. Appl. Biosci.* 9:491–497 (1993)).

Furthermore, guidance in modifying amino acid residues of SEQ ID NOS:3 or 6 while retaining activity can be provided by comparison of SEQ ID NOS:3 or 6 with the sequence of their mammalian homologs, such as homologs in non-human primates, mouse, rat, rabbit, bovine, porcine, ovine, canine or feline species, as well as sequences of their homologs in non-mammalian vertebrates, including frog Bv8 polypeptide (SEQ ID NO:11) and snake MIT1 polypeptide (SEQ ID NO:12) (see FIG. 1). It is well known in the art that evolutionarily conserved amino acid residues and domains are more likely to be important for maintaining biological activity than less well-conserved residues and domains. Thus, it would be expected that substituting a residue that is highly conserved among mammalian prokineticins, frog Bv8 polypeptide and snake MIT1 polypeptide, such as the N-terminal sequence, or any of the 10 cysteines, would likely be detrimental to activity, whereas substitution of less highly conserved residues, such as the C-terminal residues, is likely to be tolerated.

As described in the Example, retention of the six N-terminal residues (AVITGA) of prokineticin, without addition, deletion or substitution, is apparently required to retain smooth muscle contractile activity (see Table 1). However, modifications of the AVITGA sequence can result in polypeptides that do not exhibit GI smooth muscle contractile activity, but that antagonize the smooth muscle contractile activity of wild-type prokineticins. The N-terminal mutants designated SEQ ID NOS:16 and 18 are examples of modified prokineticin polypeptides with antagonistic activity.

The N-terminal domain of prokineticins, while apparently required for GI smooth muscle contractile activity, is not sufficient for GI smooth muscle contractile activity. Specifically, a prokineticin N-terminal peptide (SEQ ID NO:19), or a polypeptide with the cysteine-rich domain of prokineticin substituted with the cysteine-rich domain of either co-lipase or dickkopf4, did not exhibit smooth muscle contractile activity.

The cysteine-rich domain of prokineticins was shown to also be required for GI smooth muscle contractile activity (see Table 1). Specifically, correct cysteine pairing was shown to be required in order to retain activity, as substitutions at either of two cysteines abolished activity.

The sequence C-terminal to the final cysteine is presumably not required, as evidenced by GI smooth muscle contractile activity of prokineticin polyepeptides with a 6XHis tag inserted at this position. Additionally, as evidenced by similar activities of prokineticins 1 and 2, despite only being 44% identical, amino acid sequence substitutions at positions other than the N-terminus and conserved cysteine residues are well tolerated.

Substitutions to the amino acid sequences designated SEQ ID NOS:3 or 6 can either be conservative or non-conservative. Conservative amino acid substitutions include, but are not limited to, substitution of an apolar amino acid with another apolar amino acid (such as replacement of leucine with an isoleucine, valine, alanine, proline, tryptophan, phenylalanine or methionine); substitution of a charged amino acid with a similarly charged amino acid (such as replacement of a glutamic acid with an aspartic acid, or replacement of an arginine with a lysine or histidine); substitution of an uncharged polar amino acid with another uncharged polar amino acid (such as replacement of a serine with a glycine, threonine, tyrosine, cysteine, asparagine or glutamine); or substitution of a residue with a different functional group with a residue of similar size and shape (such as replacement of a serine with an alanine; an arginine with a methionine; or a tyrosine with a phenylalanine).

Specifically contemplated substitutions to the amino acid sequences designated SEQ ID NOS:3 and 6 include replacement of residues from wild-type prokineticin 1 with residues from prokineticin 2, and vice versa. The replacements can be of single residues, multiple residues throughout the polypeptide, or multiple contiguous residues. Because chimeras between SEQ ID NOS:3 and 6, namely SEQ ID NOS:13 and 14, were demonstrated to exhibit prolonged contractile activity in comparison with wild-type prokineticins, it is contemplated that substituted prokineticins can be potent therapeutics in vivo.

Additions to the amino acid sequence designated SEQ ID NOS:3 or 6 include, but are not limited to, the addition of "tag" sequences, which are preferably added at the C terminus. Such tag sequence include, for example, epitope tags, histidine tags, glutathione-S-transferase (GST), and the like, or sorting sequences. Such additional sequences can be used, for example, to facilitate recombinant expression, purification or characterization of a prokineticin. Exemplary polypeptides containing additions to the sequences designated SEQ ID NOS:3 or 6 are the active prokineticins prepared as described in the Example by the insertion of a 6XHis-tag after the C-terminal cysteine.

Deletions to the amino acid sequences designated SEQ ID NOS:3 or 6 include, but are not limited to, deletion of one or more residues at the C-termini that are not highly conserved among the active polypeptides shown in FIG. 1. Deleted sequences can optionally be replaced by tag sequences, as described previously.

Chemical and enzymatic modifications to the polypeptide containing the amino acid sequence designated SEQ ID NOS:3 or 6 include, but are not limited to the following: replacement of hydrogen by an alkyl, acyl, or amino group; esterification of a carboxyl group with a suitable alkyl or aryl moiety; alkylation of a hydroxyl group to form an ether derivative; phosphorylation or dephosphorylation of a serine, threonine or tyrosine residue; or N- or O-linked glycosylation.

As used herein, the term "isolated" indicates that the molecule is altered by the hand of man from how it is found in its natural environment. Preferably, an "isolated" prokineticin polypeptide can be a "substantially purified" molecule, that is at least 60%, 70%, 80%, 90 or 95% free from cellular components with which it is naturally associated. An isolated polypeptide can be in any form, such as in a buffered solution, a suspension, a lyophilized powder, recombinantly expressed in a heterologous cell, bound to a receptor or attached to a solid support.

The invention provides isolated polypeptides that stimulate gastrointestinal smooth muscle contraction. In one embodiment, the polypeptide contains an amino acid sequence at least 50% identical to the sequence of human prokineticin 1 (SEQ ID NO:3), and including the N-terminal 6 amino acids of SEQ ID NO:3, the 10 conserved cysteine residues of SEQ ID NO:3, and from 0 to 9 of the 9 C-terminal amino acids of SEQ ID NO:3. The encoded polypeptide can thus have at least 60%, 65%, 70%, 75% identity, including at least 80%, 85%, 90%, 95%, 96%, 98%, 99% or greater identity to SEQ ID NO:3. An exemplary polypeptide contains the amino acid sequence designated SEQ ID NO:3, or amino acids 1–77 thereof.

In one embodiment, the isolated polypeptide does not contain the amino acid sequence NNFGNGRQER-RKRKRSKRKKE (SEQ ID NO:7). In another embodiment, the isolated polypeptide does not contain the amino acid sequence SHVANGRQERRRAKRRKRKKE (SEQ ID NO:8).

In another embodiment, the polypeptide contains an amino acid sequence at least 50% identical to the sequence of human prokineticin 2 (SEQ ID NO:6), and including the N-terminal 6 amino acids of SEQ ID NO:6, the 10 conserved cysteine residues of SEQ ID NO:6, and from 0 to 4 of the 4 C-terminal amino acids of SEQ ID NO:6. The encoded polypeptide can thus have at least 60%, 65%, 70%, 75% identity, including at least 80%, 85%, 90%, 95%, 96%, 98%, 99% or greater identity to SEQ ID NO:6. An exemplary polypeptide contains the amino acid sequence designated SEQ ID NO:6, or amino acids 1–77 thereof.

As used herein, the term "percent identity" with respect to two molecules is intended to refer to the number of identical nucleotide or amino acid residues between the aligned portions of two sequences, expressed as a percentage of the total number of aligned residues, as determined by comparing the entire sequences using an optimized manual alignment or computer alignment, such as a BLAST 2.0 alignment (Tatusova et al., *FEMS Microbiol Lett.* 174:247–250 (1999)).

For certain applications, such as in the screening methods disclosed herein, a prokineticin polypeptide can be labeled with a detectable moiety, such as a radiolabel, a fluorochrome, a ferromagnetic substance, a luminescent tag or a detectable binding agent such as biotin. Other suitable labeled moieties are well known in the art.

The invention also provides methods for preparing an isolated prokineticin polypeptide that is able to stimulate GI smooth muscle contraction, by culturing host cells (described below) so as to express a recombinant prokineticin polypeptide, and refolding the polypeptide under conditions that minimize protein aggregation.

Recombinant expression of polypeptides containing multiple cysteine residues often results in the incorrect formation of inter- and intra-molecular disulfide bonds, which leads to the production of inactive, aggregated bacterial proteins. As disclosed herein, these problems can be overcome using conditions that minimize protein aggregation during refolding of the expressed polypeptide. Exemplary conditions that minimize protein aggregation are described in the Example, and differ from conventional conditions for preparing recombinant protein by including one or more of the following refolding conditions: 1) keeping protein concentration low (e.g. about 100 µg/ml); 2) dialysing, rather than diluting, the peptides to remove denaturing agent; 3) omitting oxidants from buffers; 4) maintaining high concentrations of urea in all buffers; 5) maintaining high concentrations of glycerol (e.g. at least about 10%) in buffers; and 6) keeping peptides and buffers at low temperature (e.g. about 4° C.). Of these conditions, it is contemplated that low protein concentration (ie. less than about 250 µg/ml, preferably less than 200 µg/ml, 150 µg/ml, 100 µg/ml, or 50 µg/ml) and high urea concentration (e.g. at least about 1.5M, such as about 2M, 4M, 6M, 8M or higher) are the most important factors in successful refolding of active prokineticins.

It is expected that the same or similar conditions as those described herein can be used to recombinantly express and refold other polypeptides containing multiple cysteines, including dickkopf, co-lipase, MIT-1 and Bv8, so as to isolate a biologically active polypeptide.

In a preferred method for preparing an isolated prokineticin polypeptide that is able to stimulate GI smooth muscle contraction, a prokineticin polypeptide is recombinantly expressed in bacteria as a fusion protein (e.g. as a GST fusion) containing a tag (e.g. a 6XHis tag), and partially purified by affinity isolation (e.g. on a nickel column). The fused polypeptide is then cleaved so as to remove the heterologous protein (e.g. using protease factor Xa cleavage between GST and prokineticin), and the prokineticin polypeptide refolded under conditions described above to minimize protein aggregation. To obtain more highly purified polypeptide, the polypeptide can further be purified by column chromatography (e.g. reverse-phase HPLC). Those skilled in the art recognize that modification to these preferred methods for recombinantly expressing, refolding and purifying active prokineticin polypeptides can readily be determined, such as employing alternative heterologous sequences, cleavable sequences, tags, host cells and buffer conditions.

Alternatively, an isolated prokineticin polypeptide can be prepared by biochemical procedures. As disclosed herein, prokineticins 1 and 2 are expressed in a variety of human tissues (see Example, and particularly FIG. 2). Therefore, an isolated prokineticin polypeptide can be isolated from tissues or cells that normally express these polypeptides, by biochemical procedures routinely used in the art, including membrane fractionation, chromatography, electrophoresis and ligand affinity methods, or using immunoaffinity methods with the prokineticin antibodies described herein. Following biochemical isolation, an inactive prokineticin can be refolded by the methods described above to restore activity.

Likewise, an isolated prokineticin polypeptide can be prepared by chemical synthesis procedures known in the art. Following chemical synthesis, an inactive prokineticin can be refolded by the methods described herein to restore activity.

If desired, such as to optimize their functional activity, selectivity, stability or bioavailability, chemically synthesized polypeptides can be modified to include D-stereoisomers, non-naturally occurring amino acids, and amino acid analogs and mimetics. Examples of modified amino acids and their uses are presented in Sawyer, *Peptide Based Drug Design,* ACS, Washington (1995) and Gross and Meienhofer, *The Peptides: Analysis, Synthesis, Biology,* Academic Press, Inc., New York (1983). For certain applications, it can also be useful to incorporate one or more detectably labeled amino acids into a chemically synthesized polypeptide or peptide, such as radiolabeled or fluorescently labeled amino acids.

The invention also provides isolated peptides containing, or consisting of, at least 10 contiguous amino acids of the amino acid sequences designated SEQ ID NOS:3 or 6 which can, but need not, be able to stimulate gastrointestinal (GI) smooth muscle contraction. Such isolated peptides are useful, for example, in preparing and purifying prokineticin antibodies of the invention. Such peptides can also act as antagonists to block signaling through a prokineticin receptor, and thus can be used in therapeutic and screening methods. An isolated prokineticin peptide can thus contain, or consist of, at least 12, 15, 20, 25 or more contiguous amino acids of SEQ ID NOS:3 or 6, including at least, or not more than, 30, 40, 50, 60, 70, 80, 81 or 86 contiguous amino acids.

In one embodiment, an isolated prokineticin peptide contains, or consists of, at least 10 contiguous residues from within amino acid residues 6 and 48 of SEQ ID NO:3. In another embodiment, an isolated prokineticin peptide contains, or consists of, at least 10 contiguous residues from within amino acid residues 6 and 48 of SEQ ID NO:6.

An isolated peptide containing at least 10 contiguous amino acids of SEQ ID NOS:3 or 6 can be immunogenic. As used herein, the term "immunogenic" refers to a peptide that either is capable of inducing prokineticin-specific antibodies, or is capable of competing with prokineticin-specific antibodies for binding to a prokineticin. Peptides that are likely to be immunogenic can be predicted using methods and algorithms known in the art and described, for example, by Irnaten et al., *Protein Eng.* 11:949–955 (1998), and Savoie et al., *Pac. Symp. Biocomput.* 1999:182–189 (1999). The immunogenicity of the peptides of the invention can be confirmed by methods known in the art.

The isolated prokineticin polypeptide and peptides of the invention can optionally be conjugated to a carrier, such as KLH, serum albumin, tetanus toxoid and the like, using standard linking techniques, to enhance their immunogenicity. Additionally or alternatively, the isolated polypeptides and peptides can be formulated with an adjuvant known in the art, such as Freund's complete or incomplete adjuvant.

An isolated prokineticin peptide of at least 10 contiguous residues can conveniently be prepared by chemical synthesis, or by chemical or enzymatic digestion of longer peptides, prepared as described above. An isolated prokineticin peptide of at least 10 contiguous residues can also be prepared recombinantly, such as fused to a protein tag. Those skilled in the art can determine an appropriate method of preparing an isolated prokineticin peptide, depending on its size, sequence, and intended application.

The invention also provides an isolated nucleic acid molecule encoding a prokineticin polypeptide that is able to stimulate GI smooth muscle contraction. The invention nucleic acid molecules are suitable for a variety of screening, therapeutic and diagnostic applications. For example, an invention nucleic acid molecule can be expressed in vitro and the encoded prokineticin polypeptide isolated. An invention nucleic acid molecule can also be expressed in vivo, to restore normal prokineticin activity in patients, or expressed in an antisense orientation to block prokineticin expression in patients in need thereof. Additionally, the invention nucleic acid molecules can be used as probes or primers to identify and isolate prokineticin-encoding nucleic acid molecules from other species, or to identify structurally related molecules. Such probes and primers are also useful diagnostically to determine normal and abnormal expression of prokineticin in human tissues, and thus to predict susceptibility to conditions associated with altered prokineticin expression.

As used herein, the term "isolated nucleic acid molecule" is intended to mean that the nucleic acid molecule is altered, by the hand of man, from how it is found in its natural environment. For example, an isolated nucleic acid molecule can be a molecule operatively linked to an exogenous nucleic acid sequence. An isolated nucleic acid molecule can also be a molecule removed from some or all of its normal flanking nucleic acid sequences.

An isolated molecule can alternatively, or additionally, be a "substantially pure" molecule, in that the molecule is at least 60%, 70%, 80%, 90 or 95% free from cellular components with which it is naturally associated. An isolated nucleic acid molecule can be in any form, such as in a buffered solution, a suspension, a lyophilized powder, attached to a solid support (e.g. as a component of a DNA array), or in a cell.

As used herein, the term "nucleic acid molecule" refers to a polynucleotide of natural or synthetic origin, which can be single- or double-stranded, can correspond to genomic DNA, cDNA or RNA, and can represent either the sense or antisense strand or both.

The term "nucleic acid molecule" is intended to include nucleic acid molecules that contain one or more non-natural nucleotides, such as nucleotides having modifications to the base, the sugar, or the phosphate portion, or having one or more non-natural linkages, such as phosphothioate linkages. Such modifications can be advantageous in increasing the stability of the nucleic acid molecule, particularly when used in hybridization applications.

Furthermore, the term "nucleic acid molecule" is intended to include nucleic acid molecules modified to contain a detectable moiety, such as a radiolabel, a fluorochrome, a ferromagnetic substance, a luminescent tag or a detectable binding agent such as biotin. Nucleic acid molecules containing such moieties are useful as probes for detecting the presence or expression of prokineticin nucleic acid molecule.

Prokineticin polypeptides that are able to stimulate GI smooth muscle contraction have been described above. Accordingly, it is routine for those skilled in the art to prepare isolated nucleic acid molecules encoding such polypeptides. Exemplary isolated nucleic acid molecules encoding a prokineticin polypeptide that is able to stimulate GI smooth muscle contraction contains, or consists of, a) the nucleotide sequences designated SEQ ID NOS:1 or 4; b) the portion of the nucleotide sequences designated SEQ ID NOS:1 or 4 that encodes SEQ ID NOS:3 or 6 (i.e. nucleotides 55–370. of the nucleotide sequence designated SEQ ID NO:1 and nucleotides 10–334 of the nucleotide sequence designated SEQ ID NO:4); c) a nucleotide sequence that encodes an active modification or active fragment of SEQ ID NOS:3 or 6; and d) a sequence that is degenerate with respect to either a), b) or c).

In one embodiment, the isolated nucleic acid molecule does not encode the amino acid sequence NNFGNGRQERRKRKRSKRKKE (SEQ ID NO:7). In another embodiment, the isolated nucleic acid molecule does not encode the amino acid sequence SHVANGRQERRRAKRRKRKKE (SEQ ID NO:8). In yet another embodiment, an isolated nucleic acid molecule encoding a prokineticin polypeptide excludes naturally occuring signal polypeptides, such as nucleic acid molecules encoding the underlined portions of the amino acid sequences shown in FIGS. 1A and 1B (MRGATRVSIMLLLVTVSDC (SEQ ID NO:9) and MRSLCCAPLLLLLLLPLLLTPPAGDA (SEQ ID NO:10)).

In certain embodiments, an isolated nucleic acid molecule encoding a prokineticin polypeptide specifically excludes nucleic acid molecules having the exact sequence of genomic fragments ESTs and cDNAs whose sequences are compiled in publically available databases, such as GenBank Accession Nos. AI277349, AA883760, AQ426386, AC068519, AC026973, AL358215 and AL390797 or sequences which encode amino acid sequences having GenBank Accession Nos. AF182066, AF182064, AF182069 and AF182065.

In one embodiment, an isolated nucleic acid molecule encoding a prokineticin polypeptide excludes mammalian sequences present in the GenBank database that contain sequences which do not encode SEQ ID NOS:3 and 6 (e.g. nucleic acid molecules that encode 5' and 3' untranslated regions, introns or other exons present on chromosomes 1 or 3).

The invention further provides an isolated nucleic acid molecule encoding a prokineticin polypeptide that is able to stimulate GI smooth muscle contraction, wherein the nucleic acid molecule is operatively linked to a promoter of gene expression. As used herein, the term "operatively linked" is intended to mean that the nucleic acid molecule is positioned with respect to either the endogenous promoter, or a heterologous promoter, in such a manner that the promoter will direct the transcription of RNA using the nucleic acid molecule as a template.

Methods for operatively linking a nucleic acid to a heterologous promoter are well known in the art and include, for example, cloning the nucleic acid into a vector containing the desired promoter, or appending the promoter to a nucleic acid sequence using PCR. A nucleic acid molecule operatively linked to a promoter of RNA transcription can be used to express prokineticin transcripts and polypeptides in a desired host cell or in vitro transcription-translation system.

The choice of promoter to operatively link to an invention nucleic acid molecule will depend on the intended application, and can be determined by those skilled in the art. For example, if a particular gene product may be detrimental to a particular host cell, it may be desirable to link the invention nucleic acid molecule to a regulated promoter, such that gene expression can be turned on or off. Alternatively, it may be preferred to have expression driven by either a weak or strong constitutive promoter. Exemplary promoters suitable for mammalian cell systems include, for example, the SV40 early promoter, the cytomegalovirus (CMV) promoter, the mouse mammary tumor virus (MMTV) steroid-inducible promoter, and the Moloney murine leukemia virus (MMLV) promoter. Exemplary promoters suitable for bacterial cell systems include, for example, T7, T3, SP6, lac and trp promoters.

The invention further provides a vector containing an isolated nucleic acid molecule encoding a prokineticin polypeptide. Exemplary vectors include vectors derived from a virus, such as a bacteriophage, a baculovirus or a retrovirus, and vectors derived from bacteria or a combination of bacterial sequences and sequences from other organisms, such as a cosmid or a plasmid. The vectors of the invention will generally contain elements such as an origin of replication compatible with the intended host cells; transcription termination and RNA processing signals; one or more selectable markers compatible with the intended host cells; and one or more multiple cloning sites. Optionally, the vector will further contain sequences encoding tag sequences, such as GST tags, and/or a protease cleavage site, such as a Factor Xa site, which facilitate expression and purification of the encoded polypeptide.

The choice of particular elements to include in a vector will depend on factors such as the intended host cells; the insert size; whether expression of the inserted sequence is desired; the desired copy number of the vector; the desired selection system, and the like. The factors involved in ensuring compatibility between a host cell and a vector for different applications are well known in the art.

In applications in which the vectors are to be used for recombinant expression of the encoded polypeptide, the isolated nucleic acid molecules will generally be operatively linked to a promoter of gene expression, as described above, which may be present in the vector or in the inserted nucleic acid molecule. An exemplary vector suitable for fusion protein expression in bacterial cells is the pGEX-3X vector (Amersham Pharmacia Biotech, Piscataway, N.J.).

Also provided are cells containing an isolated nucleic acid molecule encoding a prokineticin polypeptide. The isolated nucleic acid molecule will generally be contained within a vector. The isolated nucleic acid molecule can be maintained episomally, or incorporated into the host cell genome.

The cells of the invention can be used, for example, for molecular biology applications such as expansion, subcloning or modification of the isolated nucleic acid molecule. For such applications, bacterial cells, such as laboratory strains of E. coli, are useful, and expression of the encoded polypeptide is not required.

The cells of the invention can also advantageously be used to recombinantly express and isolate the encoded polypeptide. For such applications bacterial cells (e.g. E. coli), insect cells (e.g. Drosophila), yeast cells (e.g. S. cerevisiae, S. pombe, or Pichia pastoris), and vertebrate cells (e.g. mammalian primary cells and established cell lines; and amphibian cells, such as Xenopus embryos and oocytes). An exemplary cell suitable for recombinantly expressing prokineticin polypeptides is an E. coli BL21 cell.

The invention further provides isolated polynucleotides that contain at least 20 contiguous nucleotides from SEQ ID NOS:1 or 4, such as portions of SEQ ID NOS:1 or 4 that encode SEQ ID NOS:2, 3, 5 or 6, or from the complement thereof. The polynucleotides of the invention-are thus of sufficient length to be useful as sequencing primers, PCR primers and hybridization probes to detect or isolate nucleic acid molecules encoding prokineticin polypeptides, and are also useful as therapeutic antisense reagents to inhibit prokineticin expression. The polynucleotides of the invention can, but need not, encode prokineticin polypeptides that are able to stimulate GI smooth muscle contraction. Those skilled in the art can determine the appropriate length and sequence of a polynucleotide of the invention for a particular application.

As used herein, the term "polynucleotide" refers to a nucleic acid molecule that contains at least 20 contiguous nucleotides from the reference sequence and which may, but need not, encode a functional polypeptide. Thus, a polynucleotide of the invention can contain at least 20, 22 or 25 contiguous nucleotides, such as at least, or not more than, 30, 40, 50, 60, 70, 80, 90, 100, 125, 150, 175, 200, 250, or 300 contiguous nucleotides from SEQ ID NOS:1 or 4, or from their complement. A polynucleotide of the invention does not consist of the exact sequence of an EST present in publically available databases, including the sequences designated by GenBank Accession Nos. AI277349, AA883760, AQ426386, AC068519, AC026973, AL358215 and AL390797 or sequences which encode amino acid sequences having GenBank Accession Nos. AF182066, AF182064, AF182069 and AF182065.

For certain applications, such as for detecting prokineticin expression in a sample, it is desirable to use isolated polynucleotide molecules of the invention that specifically hybridize to a nucleic acid molecule encoding a prokineticin. The term "specifically hybridize" refers to the ability of a nucleic acid molecule to hybridize, under stringent hybridization conditions as described below, to a nucleic acid molecule that encodes a prokineticin, without hybridizing to a substantial extent under the same conditions with nucleic acid molecules that do not encode a prokineticin, such as unrelated molecules that fortuitously contain short regions of identity with a prokineticin. Thus, a nucleic acid molecule that "specifically hybridizes" is of a sufficient length and contains sufficient distinguishing sequence from a prokineticin for use in expression analysis, such as tissue blots and Northern blots (see FIG. 2).

As used herein, the term "stringent conditions" refers to conditions equivalent to hybridization of a filter-bound nucleic acid molecule to a nucleic acid in a solution containing 50% formamide, 5× Denhart's solution, 5×SSC, 0.2% SDS at 42° C., followed by washing the filter in 0.1×SSC and 0.1% SDS at 65° C. twice for 30 minutes. Equivalent conditions to the stringent conditions set forth above are well known in the art, and are described, for example in Sambrook et al., *Molecular Cloning: A Laboratory Manual,* Cold Spring Harbor Laboratory, New York (1992).

The invention further provides a kit containing a pair of polynucleotides of the invention packaged together, either in a single container or separate containers. The pair of polynucleotides are-preferably suitable for use in polymerase chain reaction (PCR) applications. Thus, the pair of polynucleotides can be used to detect or quantitate normal or abnormal expression of a nucleic acid molecule encoding a prokineticin. The pair of polynucleotides can also be used to amplify a nucleic acid molecule encoding a prokineticin, or any portion thereof, for sequencing, subcloning or for preparing sequence modifications. The kit can further contain written instructions for use of the pair of polynucleotides in PCR applications, or solutions and buffers suitable for such applications.

The isolated prokineticin nucleic acid molecules of the invention can be prepared by methods known in the art. An exemplary method for preparing an isolated prokineticin nucleic acid molecule involves amplification of the nucleic acid molecule using prokineticin-specific primers and the polymerase chain reaction (PCR). Using PCR, a prokineticin nucleic acid molecule having any desired boundaries can be amplified exponentially starting from only a few DNA or RNA molecules, such as from a single cell. PCR methods, including methods of isolating homologs of a given nucleic acid molecule in other species using degenerate primers, are well known in the art.

Alternatively, an isolated prokineticin nucleic acid molecule can be prepared by screening a library, such as a genomic library, cDNA library or expression library, with a detectable prokineticin nucleic acid molecule or with an antibody. Human libraries, and libraries from a large variety of mammalian species, are commercially available or can be produced from species or cells of interest. The library clones identified as containing a prokineticin nucleic acid molecule can be isolated, subcloned or sequenced by routine methods.

Furthermore, an isolated prokineticin nucleic acid molecule can be prepared by direct synthetic methods. For example, a single stranded nucleic acid molecule can be chemically synthesized in one piece, or in several pieces, by automated synthesis methods known in the art. The complementary strand can likewise be synthesized in one or more pieces, and a double-stranded molecule made by annealing the complementary strands. Direct synthesis is particularly advantageous for producing relatively short molecules, such as probes and primers, and also for producing nucleic acid molecules containing modified nucleotides or linkages.

The invention also provides an antibody specific for a prokineticin polypeptide or peptide, such as an antibody specific for a polypeptide having the amino acid sequence of SEQ ID NOS:3 or 6. Also provided is an antibody specific for an isolated immunogenic peptide that contains at least 10 contiguous amino acids of SEQ ID NOS:3 or 6.

The antibodies of the invention can be used, for example, to detect prokineticin expression in research and diagnostic applications. Such antibodies are also useful for identifying nucleic acid molecules that encode prokineticin polypeptides present in mammalian expression libraries, and for purifying prokineticin polypeptides by immunoaffinity methods. Furthermore, such antibodies can be administered therapeutically to bind to and block the activity of prokineticin, such as in applications in which it is desirable to inhibit GI smooth muscle contractions.

The term "antibody," as used herein, is intended to include molecules having specific binding activity for a prokineticin peptide or polypeptide of at least about $1\times10^5$ $M^{-1}$, preferably at least $1\times10^7$ $M^{-1}$, more preferably at least $1\times10^9$ $M^{-1}$. The term "antibody" includes both polyclonal and monoclonal antibodies, as well as antigen binding fragments of such antibodies (e.g. Fab, $F(ab')_2$, Fd and Fv fragments and the like). In addition, the term "antibody" is intended to encompass non-naturally occurring antibodies, including, for example, single chain antibodies, chimeric antibodies, bifunctional antibodies, CDR-grafted antibodies and humanized antibodies, as well as antigen-binding fragments thereof.

Methods of preparing and isolating antibodies, including polyclonal and monoclonal antibodies, using peptide and polypeptide immunogens, are well known in the art and are described, for example, in Harlow and Lane, *Antibodies: A Laboratory Manual,* Cold Spring Harbor Laboratory Press (1988). Non-naturally occurring antibodies can be constructed using solid phase peptide synthesis, can be produced recombinantly or can be obtained, for example, by screening combinatorial libraries consisting of variable heavy chains and variable light chains. Such methods are described, for example, in Huse et al. *Science* 246:1275–1281 (1989); Winter and Harris, *Immunol. Today* 14:243–246 (1993); Ward et al., *Nature* 341:544–546 (1989); Hilyard et al., *Protein Engineering: A practical approach* (IRL Press 1992); and Borrabeck, *Antibody Engineering,* 2d ed. (Oxford University Press 1995).

The invention provides a method of identifying a prokineticin receptor ligand. The method is practiced by contacting a preparation containing prokineticin receptor with one or more candidate compounds, and identifying a candidate compound that specifically binds the receptor. Such a compound is characterized as a prokineticin receptor ligand.

The term "ligand," as used herein, includes compounds that bind to the prokineticin receptor at the same or different site as prokineticin.

As used herein, the term "candidate compound" refers to any biological or chemical compound. For example, a candidate compound can be a naturally occurring macromolecule, such as a polypeptide, nucleic acid, carbohydrate, lipid, or any combination thereof. A candidate compound also can be a partially or completely synthetic derivative, analog or mimetic of such a macromolecule, or a small organic molecule prepared by combinatorial chemistry methods. If desired in a particular assay format, a candidate compound can be detectably labeled or attached to a solid support.

Methods for preparing large libraries of compounds, including simple or complex organic molecules, metal-containing compounds, carbohydrates, peptides, proteins, peptidomimetics, glycoproteins, lipoproteins, nucleic acids, antibodies, and the like, are well known in the art and are described, for example, in Huse, U.S. Pat. No. 5,264,563; Francis et al., *Curr. Opin. Chem. Biol.* 2:422–428 (1998); Tietze et al., *Curr. Biol.,* 2:363–371 (1998); Sofia, *Mol. Divers.* 3:75–94 (1998); Eichler et al., *Med. Res. Rev.* 15:481–496 (1995); and the like. Libraries containing large numbers of natural and synthetic compounds also can be obtained from commercial sources.

The number of different candidate compounds to test in the methods of the invention will depend on the application of the method. For example, one or a small number of candidate compounds can be advantageous in manual screening procedures, or when it is desired to compare efficacy among several predicted ligands, agonists or antagonists. However, it will be appreciated that the larger the number of candidate compounds, the greater the likelihood of identifying a compound having the desired activity in a screening assay. Additionally, large numbers of compounds can be processed in high-throughput automated screening assays. Therefore, "one or more candidate compounds" can be, for example, 2 or more, such as 5, 10, 15, 20, 50 or 100 or more different compounds, such as greater than about $10^3$, $10^5$ or $10^7$ different compounds.

A suitable preparation for a identifying a prokineticin receptor ligand can employ a tissue, cell, cell membrane, or purified prokineticin receptor, so long as the preparation contains a prokineticin receptor in a suitable conformation for binding prokineticin with a similar affinity and specificity as a prokineticin receptor expressed on GI smooth muscle tissues.

In one embodiment, the preparation is an intestinal smooth muscle preparation, such as a mammalian ileal, fundic muscle or proximal colon preparation, or membrane preparation thereof. A suitable intestinal smooth muscle preparation is a guinea pig ileal preparation prepared by the methods described in the Example.

In another embodiment, the preparation is a cell line that expresses prokineticin receptor, or membrane preparation thereof. A cell line that expresses prokineticin receptor can be identified by methods known in the art, such as the competitive binding assays described in the Example. An exemplary cell line that expresses prokineticin receptor is the melanoma cell line M2A7 (available from American Type Culture Collection as ATCC CRL-2500). Other cell lines that express prokineticin receptor include M2 melanoma cells (Cunningham et al., *Science* 255;325–327 (1992)) and RC-4B/C pituitary tumor cells (ATCC CRL-1903).

A suitable control cell line that does not express prokineticin receptor is HEK293 (available from American Type Culture Collection as CRL-1573). Other control cell include COS-7, COS-1, Ltk-, NIH3T3, C6, NS10Y and HT-29 cells.

Appropriate assays to identify receptor ligands are known in the art. Such assays can involve directly determining binding of the candidate compound to the receptor preparation. Direct assays are suitable when an appropriate control preparation is available that does not contain the prokineticin receptor. Such assays can also involve determining the ability of the candidate compound to compete with a prokineticin polypeptide for binding to the receptor preparation. Competition assays can be performed by detectably labeling a candidate compound and competing the compound with an unlabeled prokineticin polypeptide, or competing an unlabeled candidate compound with a detectably labeled prokineticin polypeptide.

As used herein, the term "detectably labeled" refers to derivation with, or conjugation to, a moiety that is detectable by any analytical means. An exemplary detectable moiety is a radioisotope (e.g. $^{14}C$, $^{131}I$, $^{32}P$ or $^{3}H$), fluorochrome (e.g. fluoroscein, green fluorescent protein), ferromagnetic substance, or luminescent substance. Methods of detectably labeling organic and inorganic compounds with such moieties are well known in the art.

An exemplary competitive binding assay suitable for detecting a prokineticin receptor ligand is described in the Example, below. Other suitable receptor binding assays, including high-throughput assays, are described, for example, in Mellentin-Micelotti et al., *Anal. Biochem.* 272:

P182–190 (1999); Zuck et al., *Proc. Natl. Acad. Sci. USA* 96:11122–11127 (1999); and Zhang et al., *Anal. Biochem.* 268;134–142 (1999).

Other suitable assays for detecting binding include, for example, scintillation proximity assays (SPA) (Alouani, *Methods Mol. Biol.* 138:135–41 (2000)), UV or chemical cross-linking (Fancy, *Curr. Opin. Chem. Biol.* 4:28–33 (2000)), competition binding assays (Yamamura et al., *Methods in Neurotransmitter Receptor Analysis,* Raven Press, New York, 1990), biomolecular interaction analysis (BIA) such as surface plasmon resonance (SPR) (Weinberger et al., *Pharmacogenomics* 1:395–416 (2000)), mass spectrometry (MS) (McLafferty et al., *Science* 284:1289–1290 (1999) and Degterev, et al., *Nature Cell Biology* 3:173–182 (2001)), nuclear magnetic resonance (NMR) (Shuker etal., *Science* 274:1531–1534 (1996), Hajduk et al., *J. Med. Chem.* 42:2315–2317 (1999), and Chen and Shapiro, *Anal. Chem.* 71:669A–675A (1999)), and fluorescence polarization assays (FPA) (Degterev et al., supra, 2001). An appropriate binding assay can be chosen depending on the nature and purity of the receptor preparation and the number and nature of the candidate compounds.

A compound that is determined to be a prokineticin receptor ligand can further be tested to determine whether it is an agonist or antagonist of prokineticin receptor. Likewise, a compound that is determined to be a prokineticin receptor ligand can further be tested to determine whether it modulates, either positively or negatively, GI smooth muscle contractility, using an in vitro or in vivo assay known in the art, such as the assays described herein.

The invention further provides a method of identifying a prokineticin receptor agonist. The method is practiced by contacting a preparation containing a prokineticin receptor with one or more candidate compounds, and identifying a compound that selectively promotes production of a prokineticin receptor signal. Such a compound is characterized as a prokineticin receptor agonist.

The invention also provides a method of identifying a prokineticin receptor antagonist. The method is practiced by contacting a preparation containing a prokineticin receptor with one or more candidate compounds in the presence of a prokineticin, and identifying a compound that selectively inhibits production of a prokineticin receptor signal. Such a compound is characterized as a prokineticin receptor antagonist. Using the invention method, prokineticin mutants designated SEQ ID NOS:16 and 18 were identified as prokineticin receptor antagonists.

The invention methods can be performed in the presence of a suitable concentration of a prokineticin, such as within 10-fold of its $EC_{50}$. Thus, an agonist that competes with prokineticin for signaling through the prokineticin receptor, or indirectly potentiates the signaling activity of prokineticin, can be readily identified. Likewise, an antagonist that prevents prokineticin from binding the prokineticin receptor, or indirectly decreases the signaling activity of prokineticin, can also be identified.

As used herein, the term "prokineticin receptor agonist" refers to a molecule that selectively activates or increases normal signal transduction through the prokineticin receptor. As used herein, the term "prokineticin receptor antagonist" refers to a compound that selectively inhibits or decreases normal signal transduction through the prokineticin receptor.

For therapeutic applications, a prokineticin receptor agonist preferably has an $EC_{50}$, and a prokineticin receptor antagonist preferably has an $IC_{50}$, of less than about $10^{-7}$ M, such as less than $10^{-8}$ M, and more preferably less than $10^{-9}$ or $10^{-10}$ M. However, depending on the stability, selectivity and toxicity of the compound, a prokineticin receptor agonist with a higher $EC_{50}$, or a prokineticin receptor antagonist with a higher $IC_{50}$, can also be useful therapeutically.

As described herein, the endogenous prokineticin receptor appears to be a G-protein coupled receptor. Signaling through the prokineticin receptor promotes intracellular calcium ion mobilization, suggesting that the prokineticin receptor normally couples to Gαq-containing G proteins. Therefore, signaling through the prokineticin receptor can be detected by any assay known in the art that detects intracellular calcium ion mobilization. Such an assay can be performed in the presence or absence of a prokineticin.

A suitable preparation for detecting calcium ion mobilization can be a tissue or cell line expressing the prokineticin receptor, such as an intestinal smooth muscle preparation, or the M2A7 cell line.

Calcium ion mobilization can conveniently be measured using detectably labeled $Ca^{2+}$ ion indicators, such as fluorescently labeled or radiolabeled indicators, and suitable detection systems. Exemplary $Ca^{2+}$ ion indicators include FLUO-3 AM, FLUO-4 AM, FURA-2, INDO-1, FURA RED, CALCIUM GREEN, CALCIUM ORANGE, CALCIUM CRIMSON, BTC, and OREGON GREEN BAPTA (see, for example, Grynkiewitz et al., *J. Biol. Chem.* 260: 3440–3450 (1985); Sullivan et al., in *Calcium Signal Protocol, Methods in Molecular Biology* 114: 125–133, Edited by David G. Lambert, Human Press, Totowa, N.J. (1999); Miyawaki et al., *Proc. Natl. Acad. Sci. USA* 96:2135–2140 (1999); and Coward et al., *Analyt. Biochem.* 270:242–248 (1999)). A suitable detection system for monitoring calcium ion mobilization is the FLIPR (Fluorometric Imaging Plate Reader) system available from Molecular Devices.

The specificity of Gα subunits for cell-surface receptors is determined by the C-terminal five amino acids of the Gα. Thus, a variety of signal transduction pathways can be assayed to determine transduction of a G-protein coupled signal by a prokineticin receptor, by recombinantly expressing a chimeric Gα containing the five C-terminal residues of a Gα known or predicted to couple to ADP-glucose receptor (such as Gαq or a promiscuous Gα such as Gα16), with the remainder of the protein corresponding to a Gα that couples to the signal transduction pathway to be assayed (e.g. Gαs, to assay increased cAMP production, or Gαq to assay intracellular $Ca^{2+}$ mobilization). Based on the known sequences of Gα subunits, nucleic acid molecules encoding chimeric Gα can be constructed and expressed by methods known in the art and described, for example, in Conklin et al., *Nature* 363:274–276 (1993), and Komatsuzaki et al., *FEBS Letters* 406:165–170 (1995).

Thus, depending on the Gα subunit endogenously or recombinantly expressed in the assay system, prokineticin receptor signals that can be determined include, but are not limited to, calcium ion mobilization; increased or decreased production or liberation of arachidonic acid, acetylcholine, diacylglycerol, cGMP, cAMP, inositol phosphate and ions; altered cell membrane potential; GTP hydrolysis; influx or efflux of amino acids; increased or decreased phosphorylation of intracellular proteins; and activation of transcription of an endogenous gene or promoter-reporter construct downstream of any of the above-described second messenger pathways.

Suitable assays for detecting agonistic and antagonistic activity of G protein coupled receptors, including high-throughput signaling assays, are well known in the art and reviewed, for example, in reviewed, for example, in Tate et al., *Trends in Biotech.* 14:426–430 (1996).

Assay methods for identifying compounds that selectively bind to or modulate signaling through a prokineticin receptor (e.g. ligands, agonists and antagonists) generally involve comparison to a control. One type of a "control" is a preparation that is treated identically to the test preparation, except the control is not exposed to the candidate compound. Another type of "control" is a preparation that is similar to the test preparation, except that the control preparation does not express the receptor, or has been modified so as not to respond selectively to prokineticin. In this situation, the response of the test preparation to a candidate compound is compared to the response (or lack of response) of the control preparation to the same compound under substantially the same reaction conditions.

A compound that is determined to be a prokineticin receptor agonist or antagonist can further be tested to determine whether it modulates, either positively or negatively, GI smooth muscle contractility, using an in vitro or in vivo assay known in the art, such as the assays described herein.

The invention also provides compositions suitable for use in assays to identify prokineticin ligands, agonists and antagonists. Suitable compositions contain a cell or tissue containing a prokineticin receptor and a prokineticin polypeptide, which optionally can be detectably labeled. An exemplary composition comprises a GI smooth muscle preparation, such as an ileal smooth muscle preparation. A further exemplary composition comprises a cell line, such as M2A7.

The prokineticin polypeptides described herein, as well as prokineticin ligands, agonists and antagonists identified by the described screening methods, are potential therapeutic compounds that can be administered to individuals with conditions associated with abnormal gastrointestinal motility, or other conditions associated with altered expression, or activity of a prokineticin or its receptor. The invention compounds can be formulated and administered in a manner and in an amount appropriate for the condition to be treated; the weight, gender, age and health of the individual; the biochemical nature, bioactivity, bioavailability and side effects of the particular compound; and in a manner compatible with concurrent treatment regimens. An appropriate amount and formulation for a particular therapeutic application in humans can be extrapolated based on the activity of the compound in the in vitro binding and signaling assays described herein, or from recognized animal models of the particular disorder.

The total amount of therapeutic compound can be administered as a single dose or by infusion over a relatively short period of time, or can be administered in multiple doses administered over a more prolonged period of time. Additionally, the compound can be administered in a slow-release matrice, which can be implanted for systemic delivery at or near the site of the target tissue. Contemplated matrices useful for controlled release of therapeutic compounds are well known in the art, and include materials such as DepoFoam™, biopolymers, micropumps, and the like.

The therapeutic compounds can be administered to a mammal by routes known in the art including, for example, intravenously, intramuscularly, subcutaneously, intraorbitally, intracapsularly, intraperitoneally, intracisternally, intraarticularly, intracerebrally, orally, intravaginally, rectally, topically, intranasally, or transdermally. Preferred routes for human administration are oral and intravenous administration, with oral routes particularly preferred.

Preferably, the therapeutic compounds are administered to a mammal as a pharmaceutical composition comprising the compound and a pharmaceutically acceptable carrier. The choice of pharmaceutically acceptable carrier depends on the route of administration of the compound and on its particular physical and chemical characteristics. Pharmaceutically acceptable carriers are well known in the art and include sterile aqueous solvents such as physiologically buffered saline, and other solvents or vehicles such as glycols, glycerol, oils such as olive oil and injectable organic esters. A pharmaceutically acceptable carrier can further contain physiologically acceptable compounds that stabilize the compound, increase its solubility, or increase its absorption. Such physiologically acceptable compounds include carbohydrates such as glucose, sucrose or dextrans; antioxidants, such as ascorbic acid or glutathione; chelating agents; and low molecular weight proteins.

For applications that require the compounds and compositions to cross the blood-brain barrier, or to cross cell membranes, formulations that increase the lipophilicity of the compound are particularly desirable. For example, the compounds of the invention can be incorporated into liposomes (Gregoriadis, *Liposome Technology*, Vols. I to III, 2nd ed. (CRC Press, Boca Raton Fla. (1993)). Liposomes, which consist of phospholipids or other lipids, are nontoxic, physiologically acceptable and metabolizable carriers that are relatively simple to make and administer.

In one embodiment, a pharmaceutical composition containing a prokineticin polypeptide or a prokineticin agonist is administered to a mammal in an effective amount to stimulate gastrointestinal motility. Impaired GI motility is a common clinical manifestation of a variety of disorders, including irritable bowel syndrome, diabetic gastroparesis, postoperational ileus, chronic constipation, and gastrointestinal reflux disease, and the compositions of the invention can thus be used to ameliorate the symptoms of such disorders.

In another embodiment, a pharmaceutical composition containing a prokineticin antagonist is administered to a mammal in an effective amount to inhibit gastrointestinal motility. Enhanced GI motility is associated with diarrhea, which is a common symptom of infectious diseases, malabsorptive disorders, inflammatory bowel disorders, and intestinal cancers, and antagonistic compositions of the invention can thus be used to ameliorate the symptoms of such disorders.

Injection of Bv8 or MIT1 into the brain ventricles of rats leads to hyperalgesia (Mollay et al., *Eur J Pharmacol.* 374:189–196 (1999)). Therefore, prokineticin antagonists (e.g. prokineticin antibodies, mutant polypeptides comprising SEQ ID NOS:16 or 18, and other compounds determined by the methods described herein) can be administered to a mammal in an effective amount to act as an analgesic (pain killer).

Those skilled in the art can determine other conditions for which it is appropriate to administer a pharmaceutical composition of the invention, and can monitor the safety and efficacy of the therapy.

Preferably, the mammal administered a pharmaceutical composition of the invention is a human, but for certain applications the mammal can alternatively be a veterinary animal or a research animal. For example, in preclinical studies, the methods of the invention can be practiced with animals that serve as credible models of human disease, such as non-human primates, pigs, dogs, cats, and rodents (e.g. rats, mice and guinea pigs). Those skilled in the art understand which animals serve as appropriate models for a human disease of interest.

The following examples are intended to illustrate but not limit the present invention.

EXAMPLE I

Identification, Preparation and Characterization of Prokineticins 1 and 2

This example shows the cloning, recombinant expression, purification and biological activities of human prokineticins 1 and 2, as well as modifications thereof.

Materials and Methods

RNA Blot

Human multiple tissue RNA blots containing normalized samples of polyA RNA were used as described by the manufacture's instructions (Clontech). The blots were probed with random primer-labeled probes (nucleotides 1–550 and 1–1178 for prokineticin 1 and prokineticin 2 cDNAs), and signals were visualized by exposing to Kodak XAR film.

Production, Refolding and Purification of Recombinant Prokineticins

The coding sequences for mature prokineticins were cloned into prokacyotic expression vector pGEX-3X (Pharmacia). The extra nucleotides between the factor Xa protease digestion site of GST (Glutathione-s-transferase) tag and mature prokineticins were removed by site-directed mutagenesis and confirmed by sequencing. To facilitate protein purification, a 6xHis-tag was added to the C-terminus so that the fusion proteins could be purified with Ni-NTA affinity chromatography (Qiagen).

The method for production of fusion proteins is as follows. The *E. coli* cells (BL21) were grown to OD 0.8 and induced with 600 nM IPTG for 2 hours at 37° C. The cells were then pelleted, washed, and lysed with buffer A (6 M guanidine hydrochloride, 100 mM $NaH_2PO_4$ and 10 mM Tris, pH 8.0). Fusion proteins were allowed to bind to Ni-NTA beads and then washed extensively with buffer C (8 M urea, 100 mM $NaH_2PO_4$, and 10 mM Tris, pH 6.3) and buffer D (8M urea, 100 mM $NaH_2PO_4$, and 10 mM Tris, pH 5.9). Fusion protein-bound beads were equilibrated with factor Xa digestion buffer (50 mM Tris, 150 nM NaCl, and 1 mM $CaCl_2$, pH 7.5). Factor Xa digestion was performed overnight at room temperature with 10 ng/μ fusion protein. Cleaved GST tag was then washed away with buffer D. Mature prokineticins were then eluted with buffer E (8 M urea, 100 mM $NaH_2PO_4$, and 10 mM Tris, pH 4.5). Fractions were analyzed by SDS-PAGE. The pooled recombinant prokineticins were then refolded as follows. Proteins were diluted to 100 μg/ml with buffer E, and dialyzed against renaturing buffer (4 M urea, 5 mM cysteine, 0.02% Tween-20, 10% glycerol, 10 mM Tris, 150 mM NaCl, 100 mM $NaH_2PO_4$, pH 8.3). New renaturing buffer (same component except 2 M urea) was then added, and dialysis was continued for four more days with at least one more change of renaturing buffer. The refolded protein was then desalted with a spin column (Qiagen) and analyzed by receptor binding or bioassay. The final purification was performed with reverse phase-HPLC (LKB). Functional proteins were eluted with 0.08% trifluoroacetic acid and 10–50% acetonitrile gradient. The elution of protein was monitored at 206 nm. Trifluoroacetic acid and acetonitrile were then evaporated by lyophilization.

Mass Spectrometry

The electrospray ionization mass spectrometry was pwformed with a 6.5 T HiResESI Fourier Transform mass spectrometer (IonSpec, Irvine, Calif.) as previously described (Li et al., *Anal. Chem.* 66:2077–2083 (1994)). Protein eluted from RP-HPLC was lyophilized and dissolved in nanopure water and then diluted to a concentration of 1 nM with methanol-water-acetic acid (49.5%:49.5%:1%, v/v/v). 100 µl of sample was infused.

Measurement of Smooth Muscle Contraction in Isolated Organ Preparations

Guinea pigs were euthanized with $CO_2$, and a section of ileum (2–3 cm) approximately 10 cm rostral to the cecum was removed. The ileum was washed clean with Krebs-Ringer bicarbonate (KRB) buffer (124 mM NaCl, 5 mM KCl, 1.3 mM $MgSO_4$, 26 nM $NaHCO_3$, 1.2 mM $KH_2PO_4$, 1.8 mm CaCl, and 10 mM glucose) and mounted longitudinally in an organ bath containing KRB buffer. Isometric contractions were measured with a force-displacement transducer and polygraph as described previously (Thomas et al., *Biochem. Pharmacol.* 51:779–788 (1993)). The ileum was allowed to incubate for 1 hr, and then three test doses of the muscarinic agonist, oxotremorine-M, were added to ensure that the contractions were reproducible and of sufficient magnitude. The ileum was washed and allowed to rest for 5 min between each test dose. The longitudinal fundic strip and the zig-zag tracheal preparation were prepared as described previously (15). Isolated colon (proximal and distal) was prepared as described (Sawyer et al., *J. Pharmacol. Exp. Ther.* 284:269–277 (1998)). Aorta and femoral artery were taken from adult rats. A 10 ml bath was used for aorta and femoral artery experiments. Tension was recorded on a Grass polygraph with initial preloads of 0.5 g for intestinal tissues and tracheal preparations and 2 g for aorta and femoral artery.

Iodination

Prokineticin 1 was iodinated by the iodogen method as described (Eraker and Speck, *Biochem. Biophys. Res. Commun.* 80:849–857 (1978)). Briefly, refolded prokineticin 1 (7.5 µg) was incubated with 50 µg of iodogen in 50 µL of 0.5 M PBS buffer, pH 7.2 for 15 minutes at room temperature. The reaction was stopped by removal of the mixture from the iodogen tube and placing it in a microfuge tube with 100 µL of PBS containing 1 mM NaI. Following the addition of 100 µL of PBS with 1 mM NaI and 0.1% BSA, the free iodine was removed by gel filtration on Bio-Gel P2 and the radioactivity was counted. Assuming all the radioactivity was incorporated into 6.0 µg prokineticin 1 recovered (80% recovery rate), specific radioactivity was calculated as 819 cpm/fmol or 372 Ci/mole.

Receptor Binding

Membranes were prepared from guinea pig ileum as described (Li et al., *Mol. Pharmacol.* 57:446–452 (2000)), except additional steps of differential centrifugation (800 g, 10,000 g, 100,000 g, 4° C., 20 min each) were applied to reduce the background binding. Incubation was performed in 4 ml in 20 mM Tris-HCl pH 7.4 buffer containing 0.1% BSA at room temperature. For saturation binding, 1.5–200 pM of labeled prokineticin 1 was used. Non-specific binding was defined in the presence of 20 nM unlabeled prokineticin 1. For displacement experiments, unlabeled protein was pre-incubated with membrane in 3 ml total reaction volume for 1 hr, then $^{125}$I-prokineticin 1 (20 pM) was added. The membrane was incubated for an additional 3 hrs at room temperature. The binding mixture was filtered through GF-C glass filters and washed with 10 ml of 20 mM Tris-HCl, pH 7.4. Radioactivity retained on filters was counted in gamma counter. The data were analyzed with the LIGAND program.

Results

Identification and Analysis of Two Mammalian Homologues for Frog Bv8 and Snake MIT1

In an effort to identify mammalian homologues of frog Bv8 and snake MIT1, multiple databases (EST and HGTS) were searched using the BLAST 2.1 algorithm (Altschul et al. *Nucleic Acids Res.* 25:3389–3400 (1997)), with their protein sequences as queries. A search of the EST database revealed the presence of two human EST sequences (ai277349 and aa883760). Sequence analysis of these two EST clones revealed that aa 883760 encodes a predicted protein (Heijne *Nucleic Acids Res.* 14:4683–4690 (1986)) with a signal peptide of 19 amino acids and a mature protein of 86 amino acids. Clone ai277349 was found to be a partial cDNA. Full-length sequence for EST clone ai277349, cloned by 5' RACE with human brain cDNA as template, was found to contain a signal peptide of 27 amino acids and a mature protein of 81 amino acids (FIG. 1). These proteins were respectively named as prokineticin 1 and prokineticin 2 (see below).

Sequence analysis reveals that prokineticin 1 and 2 have about 44% amino acid identity, including ten conserved cysteines. Both prokineticins possess about 43% identity with frog Bv8 and snake MIT1. Interestingly, the N-terminal sequences before the first cysteine (AVITGA) is completely conserved among all species (FIG. 1), suggesting the functional significance of this region. Preliminary analysis of the mouse prokineticin 1 gene indicates that the N-terminal sequence AVITG is derived from the first exon that also contains the signal peptide sequence, whereas the cysteine-rich sequences are from other exon(s).

Prokineticins are Expressed in Various Adult and Embryonic Tissues

As an initial survey of prokineticin expression, a human masterr blot was probed using fragments of human prokineticin cDNAS. Both prokineticins were widely expressed in various adult tissues, with a generally higher expression level of prokineticin 1 compared to prokineticin 2 (FIGS. 2A, 2B). The exception was found in GI tract, liver and spleen, whereas prokineticin 2 expression seemed comparable to that of prokineticin 1. The highest level of prokineticin 1 expression is found in testis and placenta. Among human fetal tissues, all showed a similar level of expression, again with an expression level of prokineticin 1 higher than that of prokineticin 2.

The expression of prokineticins in human brain was further examined by Northern blot analysis. FIG. 2D showed that prokineticin 1 mRNA size is about 1.5 kb with the highest expression in the putamen, thalamus, temporal lobe, and corpus callosum. Prokineticin 2 expression in human brain was undetectable (data not shown).

Production, Refolding and Purification of Human Prokineticins

As the N-terminal sequences were completely conserved (FIG. 1), recombinant proteins with authentic N-terminal residue were produced first as GST-fusion proteins, followed by digestion with protease factor Xa to remove the GST tag. FIG. 3 shows that a protein with correct molecular weight was produced by factor Xa digestion.

Bioassay with guinea-pig ileum preparations revealed the unfolded recombinant proteins were inactive. As NMR examination indicated that l0 cysteines of MIT1 are formed into 5 disulfide bonds (Boisbouvier et al., *J. Mol. Biol.* 283:205–219 (1998)) and these 10 cysteines are all conserved in human prokineticins, it was considered that these disulfide bonds were probably essential for protein bioactivities. Thus considerable effort was devoted to ensure proper disulfide bond formation (out of 945 possible combinations).

Initial refolding in a single dilution into refolding buffer was unsuccessful, as almost all recombinant proteins were precipitated, probably due to the formation of inter-molecular disulfide bonds. A series of modifications to control protein aggregation and to slow disulfide bond formation were then adopted. These modifications included: 1) reduction of protein concentration to 100 μg/ml or less to favor forming intra- but not inter-molecular disulfide bonds; 2) refolding proteins by dialysis method instead of direct dilution; 3) using higher levels of urea (4 M and then 2 M) in all dialysis buffers; 4) omitting oxidants cystine or oxidized glutathione from redox pairs, leaving only 5 mM cysteine or 3 mM reduced glutathione; 5) adding glycerol to further reduce protein aggregation; 6) cooling proteins and buffers to 4° C. before initiating the refolding process. These carefully controlled steps allowed the successful refolding of recombinant prokineticins with minimal protein aggregation.

The refolded proteins were finally purified by RP-HPLC (FIG. 3A, lane 5). Mass spectrometry confirmed the formation of five disulfide bonds in refolded recombinant prokineticin 1. The molecular weight of 6xHis-tagged prokineticin 1, determined with a Fourier transform mass spectrometer, was found to be 10480.30 Da (FIG. 3C). As the calculated molecular weight with all ten cysteines present in reduced form was 10490.20, five pairs of disulfide bonds were clearly formed.

Figure 4:
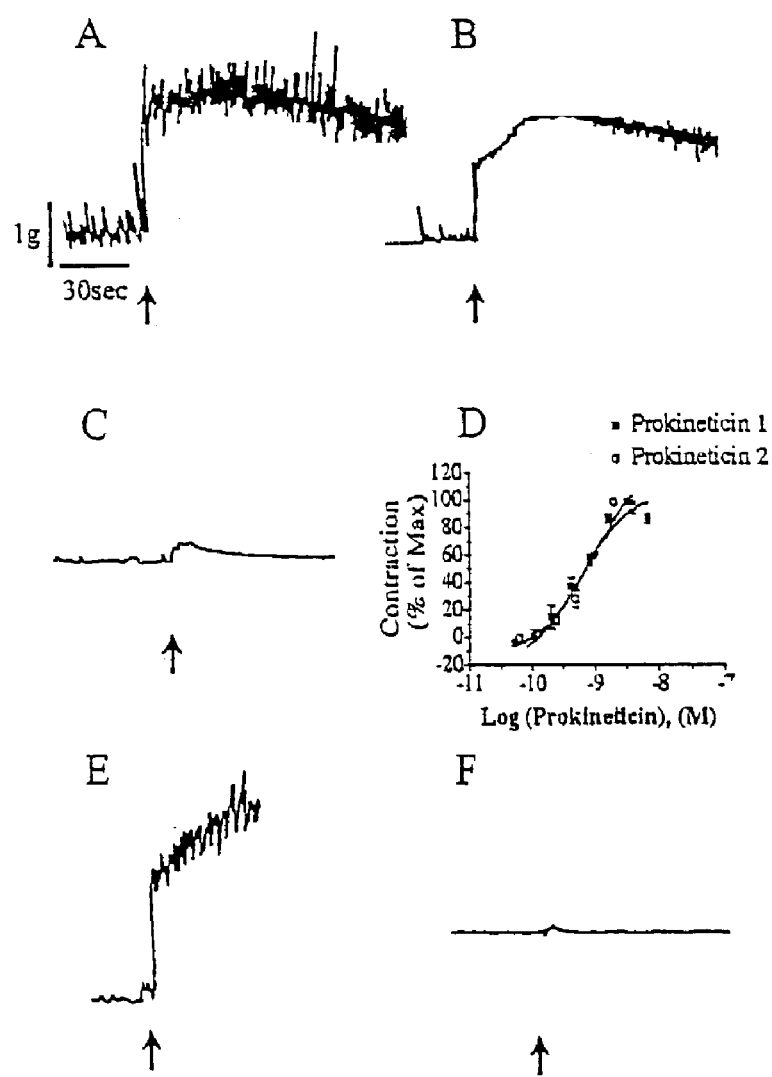
FIG. 4 shows the effects of prokineticins on the contractility of guinea-pig ileal longitudinal smooth muscle. The contractile responses to prokineticin 1 (2 nM) were measured in ileum in the absence (A) and in the presence of tetrodotoxin (0.1 μM; B) and verapamil (1 μM; C).

Refolded Recombinant Prokineticins Potently Contract Gastrointestinal Smooth Muscle The refolded recombinant prokineticins were then tested on isolated smooth muscle preparations. FIG. 4 shows that both recombinant prokineticin 1 and prokineticin 2 potently stimulated the contraction of guinea-pig ileum longitudinal muscle with ED50 values of about 0.46 and 0.90 nM, respectively. Prokineticin 1 (5 nM) also stimulated the contraction of fundic muscle strip and proximal colon, but had no effect on distal colon (25 nM, data not shown). Recombinant prokineticin 1 (25 nM) also had no effect on other smooth muscle tissues, including aorta and femoral artery, trachea and gallbladder. Thus, the contractile effect of prokineticins appears to be specific for GI smooth muscle.

To probe the possible signaling mechanisms of prokineticins, a number of kinase and ion channel inhibitors were tested. Tetrodotoxin (TTX), which is known to block nerve action potential propagation, had no effect on prokineticin 1-stimulated ileum longitudinal muscle contraction (FIG. 4B), indicating that prokineticin 1 acts directly on the smooth muscle. The contractile mechanism of prokineticin was further investigated with a number of compounds, including the protein kinase C inhibitor calphostin C (1 μM), the phospholipase A2 inhibitor 7, 7-dimethyl-(5Z,8Z)-eicosa-dienoic acid (10 μM), the tyrosine kinase inhibitor genistein (5 μM), the MEK inhibitor PD 098059 (10 μM) and L-type calcium channel blocker verapamil. Only verapamil was effective, with 1 μM completely inhibiting the contractile effect of 2 nM prokineticin I (FIG. 4C). The same concentration of verapamil also completely blocked the contractile action of 100 nM oxotremorine-M (FIG. 4F). This result indicates that, like muscarinic M3 receptor mediated contraction of the ileum (Eglen et al., *Pharmacol. Rev.* 48:531–565 (1996) and Ehlert et al., Muscurinic Receptors and Gastrointestinal Smooth Muscle, ed. Eglen, CRC Press, pgs 92–147 (1997)), calcium entry via the voltage-gated calcium channel is an essential component of prokineticin signaling.

Bioactivities of Prokineticins are Mediated by Membrane Receptors

The potent contractile action of recombinant prokineticins on guinea-pig GI smooth muscle and the inhibitory effect of the calcium channel blocker verapamil suggest a receptor-mediated mechanism for prokineticins. To provide direct evidence that prokineticins are interacting with selective membrane receptors, recombinant prokineticin was labeled with $^{125}$I and receptor binding experiments were carried out.

Scatchard analysis indicated that the specific binding of prokineticin 1 was best fitted with two-site model (F=38.78, P<0.001 versus one site model; FIG. 5A). The high- and low-affinity constants ($K_d$) were 5.0±0.8 pM and 227±63 pM (n=3), respectively. The $B_{max}$ for high- and low-affinity sites were 7.8±1.2 and 26.4±8.4 fmol/mg of protein, respectively (n=3). Competition experiments revealed that the specific binding was displaced by recombinant prokineticin 1. The displacement curves were also best fitted with two-site model (with $K_i$ of 8.0±3.9 pM, and 1.50±0.9 nM, n=3 for high- and low-affinity sites, respectively) (FIG. 5B). FIG. 5B also shows that prokineticin 2 displaced labeled prokineticin 1 with similar affinity ($K_i$ of 4.2 pM for high affinity and 1.22 nM for low affinity site, average of two experiments).

Because agonist binding to many G protein-coupled receptors is inhibited by GTP, it was investigated whether GTPγS had any effect on specific $^{125}$I-labeled prokineticin 1 binding. As shown in FIG. 5B, GTPγS caused a concentration-dependent inhibition of $^{125}$I-prokineticin 1 binding. At the highest concentration tested (10 μM), GTPγS displaced 85% of the specific prokineticin binding to ileal membranes. These results suggest that prokineticin receptor(s) belong to the G protein-coupled receptor family.

Stability of Prokineticins

Experiments were also performed to determine the half-life of prokineticins. The half-life of intravenously injected iodinated human prokineticin 1 was approximately 3 hours, compared to 10 min for motilin, a small peptide that also increases GI motility. A reasonably long half-life in the blood circulation is crucial for achieving therapeutic effect. Therefore, prokineticins are likely to be effective as therapeutics.

Structure/Activity Relationship Studies of Prokineticins

Sequence analysis indicated that prokineticins may contain two functional domains, namely the short N-terminus and the cysteine-rich C-terminus. As the N-terminal sequences preceding the first cysteine are completely conserved among prokineticins (FIG. 1), it was predicted that this region has functional importance.

In addition to prokineticins, the ten-cysteine motif is also found in a number of secreted proteins, including colipase, a cofactor for intestinal lipid digestive enzyme lipase, and dickkopfs, a family of proteins that have an important role in early embryonic development.

A number of N-terminal substitution, deletion, and insertion mutants were constructed, and recombinant, refolded proteins produced. Bioassays with ileal smooth muscle preparations revealed that these mutant proteins at concentrations up to 250 nM are not able to elicit contractions (Table 1). However, an N-terminal deletion mutant (SEQ ID NO:16) and an N-terminal insertion mutant (SEQ ID NO:18) were able to weakly antagonize the contractile effect of prokineticin 1. Therefore, N-terminal variants of prokineticins, such as SEQ ID NOS:16 and 18, are potential therapeutics for inhibiting GI contractility.

TABLE 1

|  | Polypeptide | Contractile Activity | Antagonistic Activity |
|---|---|---|---|
| Wild Type (SEQ ID NO:3) | AVITGA[Prokineticin 1] | + | − |
| Insertion (SEQ ID NO:15) | GILAVITGA[Prokineticin 1] | − | ND |
| Deletion (SEQ ID NO:16) | VITGA[Prokineticin 1] | − | + |
| Substitution (SEQ ID NO:17) | AAAAAA[Prokineticin 1] | − | ND |
| Insertion (SEQ ID NO:18) | MAVITGA[Prokineticin 1] | − | + |
| Chimera | AVITGA[Co-lipase] | − | − |
| Chimera | AVITGA[dickkopf4] | − | ND |
| peptide (SEQ ID NO:19) | AVITGACERDVQCG | − | − |
| Cys mutation | AVITGA[Prokineticin 1]18S | − | − |
| Cys mutation | AVITGA[Prokineticin 1]60R | − | − |

Chimeric recombinant proteins containing N-terminal sequences from prokineticin 1 and the C-terminal ten-cysteine domain from either colipase or Dickkopf 4 were also constructed. These two chimeric recombinant proteins were non-functional when tested with ileal smooth muscle preparation at concentrations up to 250 nM. Also tested was an N-terminal peptide (SEQ ID NO:19), which also was non-functional.

These results indicate that both N-terminal conserved sequence and C-terminal cysteine-rich domain are essential for the contractile activity of prokineticins.

Chimeric Prokineticins

A search of the draft human genome database with prokineticin cDNAs as queries revealed that genes encoding prokineticin 1 and 2 are composed of three exons. The signaling peptide and N-terminal conserved AVITG sequence are encoded in the first exon, while the cysteine-rich domain is encoded by exons 2 and 3. The 21 amino acid insertion of prokineticin 2 is encoded by an alternatively spliced mini-exon. To explore the functional difference of prokineticin 1 and 2, chimeric polypeptides were made with their exons 3 swapped (see FIG. 6). The chimeric polypeptides were designated chimera 12 (SEQ ID NO:13) and chimera 21 (SEQ ID NO:14), designating the swapped exons, as shown in FIG. 6.

Functional assays of refolded chimeric prokineticins 12 and 21 indicated that both of these chimeric polypeptides are active in contracting GI smooth muscle (FIG. 7A). However, the $EC_{50}$ for the chimeric prokineticin 21 (SEQ ID NO:14) was about 8-fold higher than prokineticin 1 or prokineticin 2. Additionally, although the peak contractions were not affected, chimeric prokineticin polypeptides resulted in prolonged contraction of ileal strips (FIG. 7B). For wild type prokineticins, the time constants to midway contraction (half way from peak contraction to sustained plateau) were about 15 mins. In contrast, for the chimeric polypeptides, these time constants were prolonged to about 40 mins.

These results suggest that the chimeric prokineticins interact slightly differently with the receptor than wild type prokineticins, and cause less pronounced tachyphylaxis.

Thus, the chimeric prokineticins (SEQ ID NOS:13 and 14) may have more potent pharmacological activity in vivo than wild-type prokineticins.

Effects of Prokineticin on Guinea Pig Ileum Smooth Muscle in Vivo

To monitor the effects of prokineticin on the contraction of ileal smooth muscle in vivo, extraluminal force transducers were implanted on the serosal surface of the guinea pig ileum. Recombinant prokineticin 1 was then administered as a bolus into the jugular vein over a 10-second period. As shown in FIG. 8, an intravenous bolus of prokineticin 1 contracts guinea pig ileal smooth muscle in a dose-dependent manner. The threshold dose of prokineticin 1 is about 0.03 μg/kg, and a dose of 30 μg/kg produces the maximum effect.

Therefore, prokineticins, demonstrated above to be able to contract ileal smooth muscle in ex vivo preparations, are also effective in vivo.

Prokineticin Signal Transduction

To probe the potential signaling mechanisms of prokineticins, cell lines were identified that express prokineticin receptor endogenously. Over twenty cell lines were screened for binding to iodinated prokineticin 1. One cell line, M2A7 melanoma cells (ATCC CRL-2500; Cunningham et al., Science 255;325–327 (1992)), clearly displayed specific binding, with a receptor level of about 150 fmole/mg protein. Other cell lines that specifically bound prokineticin included M2 melanoma cells (Cunningham et al., Science 255;325–327 (1992)) and RC-4B/C pituitary tumor cells (ATCC CRL-1903). Cell lines that did not bind prokineticin included HEK293, COS-7, COS-1, Ltk-, NIH3T3, C6, NS10Y and HT-29 cells.

To assess signaling in M2A7 cells, cytosolic calcium was measured by fura-3 fluorescence using a FLIPR system (Fluorometric Imaging Plate Reader; Molecular Devices). Cells were suspended in HEPES medium and incubated with 2 μM of fura-3 AM for 20 min at 31° C. The cells were then centrifuged, washed, resuspended in fura-3-free medium and seeded into 96 wells at $4 \times 10^4$ cells per well. The cells were loaded with Fluo-3 AM (Molecular Probes) in standard buffer solution (130 mM NaCl, 2 mM $CaCl_2$, 5 mM KCl, 10 mM glucose, 0.45 mM $KH_2PO_4$, 0.4 mM $Na_2HPO_4$, 8 mM $MgSO_4$, 4.2 mM $NaHCO_3$, 20 mM HEPES and 10 μM probenecid) with 0.1% fetal bovine serum for 1 h at 37° C., then washed with standard buffer solution. Transient changes in $[Ca_{2+}]_i$ evoked by prokineticin (0.01, 0.1, 0.3, 1, 3, 10, 100 nM) were monitored using the FLIPR system in 96-well plates at 488 nm for 210 s.

Figure 9:
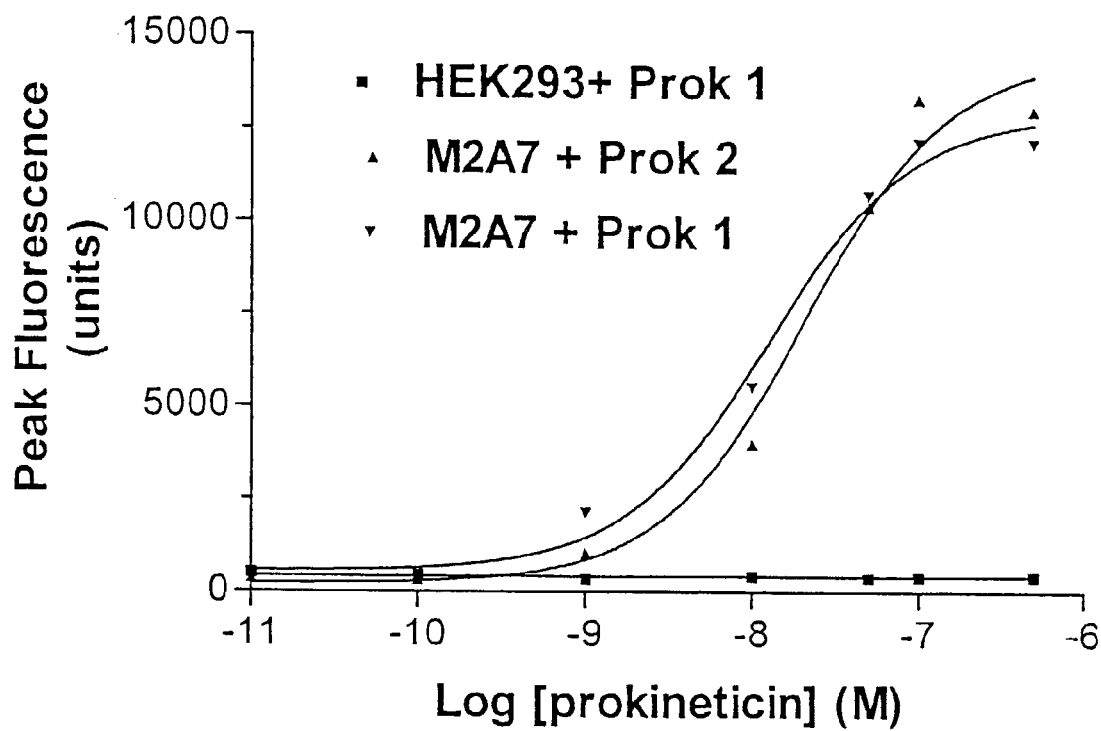
FIG. 9 shows calcium mobilization, as determined in a FLIPR assay, elicited in HEK293 or M2A7 cells by the indicated concentrations of prokineticin 1 or prokineticin 2.

As shown in FIG. 9, prokineticins can mobilize calcium in M2A7 melanoma cells, with $EC_{50}$ of about 12 and 21 nM for recombinant prokineticin 1 and prokineticin 2, respectively. The signaling is specific, as there was no response in HEK 293 cells. The calcium signaling mobilized by prokineticins is comparable to calcium signal activated by control MCH (melanin-concentrating hormone) receptor SLC1 (Saito et al., Nature 400:265–269 (1999)). The calcium signals elicited by prokineticins are more much robust than the modest calcium signal induced by activation of a typical receptor tyrosine kinase. This result is consistent with the observation, described above, that the tyrosine protein kinase inhibitor genistein (5 mM) had no effect on the contractile activity of prokineticin on ileal smooth muscle.

These results indicate that the prokineticin receptor(s) is/are likely to be GPCR(s), and to signal through Gαq.

Discussion

The results described above establish the existence of mammalian homologues of frog BV8 and snake MIT1. To reflect their potent and specific effects on GI smooth muscle, these proteins have been named prokineticins. Their high potency in specifically stimulating the contraction of guinea-pig ileum smooth muscle but not other smooth muscles including aorta, femoral artery, trachea, and gallbladder indicate that prokineticins may be important endogenous regulators of GI motility. Prokineticins may regulate GI smooth muscle as neurocrine signaling molecules, or circulating hormones, or paracrine humoral agents. Since prokineticins are also widely expressed outside the GI system, it is possible that prokineticins may be released from remote organs and regulate GI activity. In this respect, it has also been determined that prokineticins are resistant to protease treatment, which supports their potential long-range and long-term effects.

The molecular size and the processing of prokineticins distinguish them from typical neuropeptides, and indicate they are more similar to cytokines. As one mechanism for eliminating pathogenic organisms is to enhance motility and push the offending organisms out of the GI tract, prokineticins may also be part of defending immune response, i.e. functioning as inflammatory cytokines that increase the GI motility.

The high potency of recombinant prokineticins on GI contractility suggests that prokineticins probably interact with cell surface receptor(s). This conclusion is reinforced by the receptor binding experiments described above, which demonstrate a saturably high affinity for the iodinated recombinant prokineticin. Moreover, the observation that 10 μM GTPγS can displace almost all of the specific binding indicates the involvement of G protein in prokineticin receptor signaling. Furthermore, the inhibitory effect of the calcium channel blocker verapamil on the contractile effect of prokineticin is consistent with a receptor-mediated mechanism for prokineticins, and also suggests a similar signaling mechanism of prokineticins as those of the M3 muscarinic and motilin receptor in contracting GI smooth muscle: calcium entry via voltage-gated calcium channel is an essential component. Thus, prokineticin receptor most likely is a G protein coupled receptor.

However, alternative interpretations are possible. For instance, prokineticins may cause smooth muscle contraction by directly activating non-selective cation ion channels, or blocking inhibitory potassium channels on GI smooth muscle cells.

Sequence analysis indicates that prokineticins may contain two functional domains: the short N-terminus and the cysteine-rich C-terminus. Since the N-terminal sequences preceding the first cysteine are completely conserved among prokineticins (FIG. 1), this region is likely to have functional importance. In addition to prokineticins and their isoforms from other species, a similar ten-cysteine motif is also found in a number of other secreted proteins, including colipase, a cofactor for intestinal lipid digestive enzyme lipase (van Tilbeurgh et al., *Nature* 359:159–162 (1992)) and dikkopfs, a family of proteins that have important roles in early embryonic development (Glinka et al., *Nature* 391:357–362 (1998) and Aravind et al., *Curr. Biol.* 8:R477–478 (1998)). Interestingly, dickkopfs actually possess two ten-cysteine domains that have mirror symmetry. X-ray crystallography and solution structural analysis have demonstrated that MIT1is formed of five pairs of disulfide bonds and folded into a structure similar to colipase (Boisbouvier et al., *J. Mol. Biol.* 283:205–219 (1998)).

Successful refolding of proteins with five pairs of disulfide bonds has not hitherto been accomplished in vitro. Refolding of proteins with more than three pairs of disulfide bonds is still regarded as challenging and difficult (Georgiou et al., *Curr. Opin. Biotechnol.* 7:190–197 (1996) and Lihe et al., *Curr. Opin. Biotechnol.* 9:497–501 (1998)). The expression of such disulfide bond-rich proteins in *E. Coli* often results in no formation of disulfide bonds, or more probably the formation of incorrect intramolecular or intermolecular disulfide bonds. These events routinely lead to production of inactive recombinant proteins and their aggregation in bacterial inclusion bodies.

In this study, a slow exchange method was utilized to refold prokineticins that have five pairs of disulfide bonds. A number of factors eventually contributed to the successful refolding of prokineticins: 1) a slow rate of removal of denaturing agent; 2) using only reducing agents in the redox refolding mixture, allowing slow formation of disulfide bonds; 3) low temperature; 4) high concentration of urea and glycerol in dialyzing buffer to prevent protein aggregation; 5) low concentration of recombinant protein to favor forming intra- but not inter-molecular disulfide bonds. These refolding conditions can be used to design protocols for refolding other recombinant proteins that possess multiple disulfide bonds.

In summary, cDNAs encoding two prokineticins have been described. Refolded recombinant prokineticins potently and specifically stimulate the contraction of GI smooth muscle. As impaired GI motility is a very common clinical manifestation in many common disorders including irritable bowel syndrome, diabetic gastroparesis, postoperational ileus, chronic constipation, and gastroesophageal reflux disease (Longo et al., *Dis Colon Rectum* 36:696–708 (1993); Tonini, *Pharmacol. Res.* 33:217–226 (1996); Samsom and Smout, *Dig Dis.* 15:263–274 (1998); Achem and Robinson, *Dig Dis.* 16:38–46 (1998) and Briejer et al., *Trends Pharmacol Sci.* 20:1–3 (1999)), the discovery of endogenous regulators of GI smooth muscle should facilitate the development of novel therapeutics for such disorders that will benefit from altered GI motility.

All journal article, reference and patent citations provided above, in parentheses or otherwise, whether previously stated or not, are incorporated herein by reference in their entirety.

Although the invention has been described with reference to the examples provided above, it should be understood that various modifications can be made without departing from the spirit of the invention.

What is claimed is:

1. A method of stimulating the gastrointestinal motility in a mammal, comprising administering to the mammal an effective amount of an isolated chimeric prokineticin polypeptide having an amino acid sequence as set forth in SEQ ID NO:13 or 14.

2. The method of claim 1, wherein the gastrointestinal motility is gastrointestinal contractions.

3. The method of claim 1, wherein the contractions are prolonged as compared to contractions after administration of prokineticin SEQ ID NO: 3 or 6.

SEQUENCE LISTING

```
<160> NUMBER OF SEQ ID NOS: 19

<210> SEQ ID NO 1
<211> LENGTH: 1377
<212> TYPE: DNA
<213> ORGANISM: Homo sapiens
```

```
<220> FEATURE:
<221> NAME/KEY: CDS
<222> LOCATION: (55)...(369)

<400> SEQUENCE: 1
ggggaagcga gaggcatcta agcaggcagt gttttgcctt caccccaagt gacc atg        57
                                                            Met
                                                            1 aga ggt gcc acg cga gtc tca atc atg ctc ctc cta gta act gtg tct       105
Arg Gly Ala Thr Arg Val Ser Ile Met Leu Leu Leu Val Thr Val Ser
        5                  10                  15 gac tgt gct gtg atc aca ggg gcc tgt gag cgg gat gtc cag tgt ggg       153
Asp Cys Ala Val Ile Thr Gly Ala Cys Glu Arg Asp Val Gln Cys Gly
 20                  25                  30 gca ggc acc tgc tgt gcc atc agc ctg tgg ctt cga ggg ctg cgg atg       201
Ala Gly Thr Cys Cys Ala Ile Ser Leu Trp Leu Arg Gly Leu Arg Met
 35                  40                  45 tgc acc ccg ctg ggg cgg gaa ggc gag gag tgc cac ccc ggc agc cac       249
Cys Thr Pro Leu Gly Arg Glu Gly Glu Glu Cys His Pro Gly Ser His
 50                  55                  60                  65 aag gtc ccc ttc ttc agg aaa cgc aag cac cac acc tgt cct tgc ttg       297
Lys Val Pro Phe Phe Arg Lys Arg Lys His His Thr Cys Pro Cys Leu
                 70                  75                  80 ccc aac ctg ctg tgc tcc agg ttc ccg gac ggc agg tac cgc tgc tcc       345
Pro Asn Leu Leu Cys Ser Arg Phe Pro Asp Gly Arg Tyr Arg Cys Ser
                 85                  90                  95 atg gac ttg aag aac atc aat ttt taggcgcttg cctggtctca ggatacccac      399
Met Asp Leu Lys Asn Ile Asn Phe
            100                 105 catccttttc tgagcacagc ctggattttt atttctgcca tgaaacccag ctcccatgac     459
tctcccagtc cctacactga ctaccctgat ctctcttgtc tagtacgcac atatgcacac     519
aggcagacat acctcccatc atgacatggt ccccaggctg gcctgaggat gtcacagctt     579
gaggctgtgg tgtgaaaggt ggccagcctg gttctcttcc ctgctcaggc tgccagagag     639
gtggtaaatg gcagaaagga cattcccccct ccctcccca ggtgacctgc tctctttcct     699
gggccctgcc cctctcccca catgtatccc tcggtctgaa ttagacattc ctgggcacag     759
gctcttgggt gcattgctca gagtcccagg tcctggcctg accctcaggc ccttcacgtg     819
aggtctgtga ggaccaattt gtgggtagtt catcttccct cgattggtta actccttagt     879
ttcagaccac agactcaaga ttggctcttc ccagagggca gcagacagtc accccaaggc     939
aggtgtaggg agcccaggga ggccaatcag cccccctgaag actctggtcc cagtcagcct    999
gtggcttgtg gcctgtgacc tgtgaccttc tgccagaatt gtcatgcctc tgaggccccc   1059
tcttaccaca ctttaccagt taaccactga agccccaat tcccacagct tttccattaa    1119
aatgcaaatg gtggtggttc aatctaatct gatattgaca tattagaagg caattagggt    1179
gtttccttaa acaactcctt tccaaggatc agccctgaga gcaggttggt gactttgagg    1239
agggcagtcc tctgtccaga ttggggtggg agcaagggac agggagcagg gcagggctg    1299 aaagggcac tgattcagac cagggaggca actacacacc aacctgctgg ctttagaata    1359
aaagcaccaa ctgaactg                                                 1377

<210> SEQ ID NO 2
<211> LENGTH: 105
<212> TYPE: PRT
<213> ORGANISM: Homo sapiens

<400> SEQUENCE: 2
```

```
Met Arg Gly Ala Thr Arg Val Ser Ile Met Leu Leu Val Thr Val
 1               5                  10                  15

Ser Asp Cys Ala Val Ile Thr Gly Ala Cys Glu Arg Asp Val Gln Cys
                 20                  25                  30

Gly Ala Gly Thr Cys Cys Ala Ile Ser Leu Trp Leu Arg Gly Leu Arg
             35                  40                  45

Met Cys Thr Pro Leu Gly Arg Glu Gly Glu Cys His Pro Gly Ser
 50                  55                  60

His Lys Val Pro Phe Phe Arg Lys Arg Lys His His Thr Cys Pro Cys
 65                  70                  75                  80

Leu Pro Asn Leu Leu Cys Ser Arg Phe Pro Asp Gly Arg Tyr Arg Cys
                 85                  90                  95

Ser Met Asp Leu Lys Asn Ile Asn Phe
                100                 105

<210> SEQ ID NO 3
<211> LENGTH: 86
<212> TYPE: PRT
<213> ORGANISM: Homo sapiens

<400> SEQUENCE: 3

Ala Val Ile Thr Gly Ala Cys Glu Arg Asp Val Gln Cys Gly Ala Gly
 1               5                  10                  15

Thr Cys Cys Ala Ile Ser Leu Trp Leu Arg Gly Leu Arg Met Cys Thr
                 20                  25                  30

Pro Leu Gly Arg Glu Gly Glu Cys His Pro Gly Ser His Lys Val
             35                  40                  45

Pro Phe Phe Arg Lys Arg Lys His His Thr Cys Pro Cys Leu Pro Asn
 50                  55                  60

Leu Leu Cys Ser Arg Phe Pro Asp Gly Arg Tyr Arg Cys Ser Met Asp
 65                  70                  75                  80

Leu Lys Asn Ile Asn Phe
                 85

<210> SEQ ID NO 4
<211> LENGTH: 1406
<212> TYPE: DNA
<213> ORGANISM: Homo sapiens
<220> FEATURE:
<221> NAME/KEY: CDS
<222> LOCATION: (10)...(333)

<400> SEQUENCE: 4 gagggcgcc atg agg agc ctg tgc tgc gcc cca ctc ctg ctc ctc ttg ctg      51
          Met Arg Ser Leu Cys Cys Ala Pro Leu Leu Leu Leu Leu Leu
           1               5                  10 ctg ccg ccg ctg ctg ctc acg ccc cgc gct ggg gac gcc gcc gtg atc       99
Leu Pro Pro Leu Leu Leu Thr Pro Arg Ala Gly Asp Ala Ala Val Ile
 15                  20                  25                  30 acc ggg gct tgt gac aag gac tcc caa tgt ggt gga ggc atg tgc tgt      147
Thr Gly Ala Cys Asp Lys Asp Ser Gln Cys Gly Gly Gly Met Cys Cys
                 35                  40                  45 gct gtc agt atc tgg gtc aag agc ata agg att tgc aca cct atg ggc      195
Ala Val Ser Ile Trp Val Lys Ser Ile Arg Ile Cys Thr Pro Met Gly
             50                  55                  60 aaa ctg gga gac agc tgc cat cca ctg act cgt aaa gtt cca ttt ttt      243
Lys Leu Gly Asp Ser Cys His Pro Leu Thr Arg Lys Val Pro Phe Phe
 65                  70                  75
```

```
ggg cgg agg atg cat cac act tgc cca tgt ctg cca ggc ttg gcc tgt       291
Gly Arg Arg Met His His Thr Cys Pro Cys Leu Pro Gly Leu Ala Cys
 80                  85                  90 tta cgg act tca ttt aac cga ttt att tgt tta gcc caa aag               333
Leu Arg Thr Ser Phe Asn Arg Phe Ile Cys Leu Ala Gln Lys
 95                 100                 105 taatcgctct ggagtagaaa ccaaatgtga atagccacat cttacctgta aagtcttact     393
tgtgattgtg ccaaacaaaa aatgtgccag aaagaaatgc tcttgcttcc tcaactttcc     453
aagtaacatt tttatctttg atttgtaaat gatttttttt tttttttta tcgaaagaga      513
attttacttt tggatagaaa tatgaagtgt aaggcattat ggaactggtt cttatttccc     573
tgtttgtgtt ttggtttgat ttggcttttt tcttaaatgt caaaacgta cccatttca       633
caaaatgag gaaataaga atttgatatt ttgttagaaa acttttttt tttttttctc        693
accaccccaa gccccatttg tgccctgccg cacaaataca cctacagctt ttggtcccctt    753
gcctcttcca cctcaaagaa tttcaaggct cttaccttac tttattttg tccatttctc      813
ttccctcctc ttgcatttta aagtggaggg tttgtctctt tgagtttgat ggcagaatca     873
ctgatgggaa tccagctttt tgctggcatt taaatagtga aaagagtgta tatgtgaact     933
tgacactcca aactcctgtc atggcacgga agctaggagt gctgctggac ccttcctaaa     993
cctgtcactc aagaggactt cagctctgct gttgggctgg tgtgtggaca gaaggaatgg    1053
aaagccaaat taatttagtc cagatttcta ggtttgggtt tttctaaaaa taaaagatta   1113
catttacttc ttttactttt tataaagttt tttttcctta gtctcctact tagagatatt    1173
ctagaaaatg tcacttgaag aggaagtatt tattttaatc tggcacaaca ctaattacca   1233
tttttaaagc ggtattaagt tgtaatttaa accttgtttg taactgaaag gtcgattgta   1293
atggattgcc gtttgtacct gtatcagtat tgctgtgtaa aaattctgta tcagaataat   1353
aacagtactg tatatcattt gatttatttt aatattatat ccttattttt gtc           1406

<210> SEQ ID NO 5
<211> LENGTH: 108
<212> TYPE: PRT
<213> ORGANISM: Homo sapiens

<400> SEQUENCE: 5

Met Arg Ser Leu Cys Cys Ala Pro Leu Leu Leu Leu Leu Leu Leu Pro
 1               5                  10                  15

Pro Leu Leu Thr Pro Arg Ala Gly Asp Ala Ala Val Ile Thr Gly
            20                  25                  30

Ala Cys Asp Lys Asp Ser Gln Cys Gly Gly Met Cys Cys Ala Val
         35                  40                  45

Ser Ile Trp Val Lys Ser Ile Arg Ile Cys Thr Pro Met Gly Lys Leu
 50                  55                  60

Gly Asp Ser Cys His Pro Leu Thr Arg Lys Val Pro Phe Phe Gly Arg
 65                  70                  75                  80

Arg Met His His Thr Cys Pro Cys Leu Pro Gly Leu Ala Cys Leu Arg
                 85                  90                  95

Thr Ser Phe Asn Arg Phe Ile Cys Leu Ala Gln Lys
            100                 105

<210> SEQ ID NO 6
<211> LENGTH: 81
<212> TYPE: PRT
<213> ORGANISM: Homo sapiens
```

-continued

```
<400> SEQUENCE: 6

Ala Val Ile Thr Gly Ala Cys Asp Lys Asp Ser Gln Cys Gly Gly Gly
1               5                   10                  15

Met Cys Cys Ala Val Ser Ile Trp Val Lys Ser Ile Arg Ile Cys Thr
            20                  25                  30

Pro Met Gly Lys Leu Gly Asp Ser Cys His Pro Leu Thr Arg Lys Val
        35                  40                  45

Pro Phe Phe Gly Arg Arg Met His His Thr Cys Pro Cys Leu Pro Gly
    50                  55                  60

Leu Ala Cys Leu Arg Thr Ser Phe Asn Arg Phe Ile Cys Leu Ala Gln
65                  70                  75                  80

Lys

<210> SEQ ID NO 7
<211> LENGTH: 21
<212> TYPE: PRT
<213> ORGANISM: Homo sapiens

<400> SEQUENCE: 7

Asn Asn Phe Gly Asn Gly Arg Gln Glu Arg Arg Lys Arg Lys Arg Ser
1               5                   10                  15

Lys Arg Lys Lys Glu
            20

<210> SEQ ID NO 8
<211> LENGTH: 21
<212> TYPE: PRT
<213> ORGANISM: Homo sapiens

<400> SEQUENCE: 8

Ser His Val Ala Asn Gly Arg Gln Glu Arg Arg Arg Ala Lys Arg Arg
1               5                   10                  15

Lys Arg Lys Lys Glu
            20

<210> SEQ ID NO 9
<211> LENGTH: 19
<212> TYPE: PRT
<213> ORGANISM: Homo sapiens

<400> SEQUENCE: 9

Met Arg Gly Ala Thr Arg Val Ser Ile Met Leu Leu Leu Val Thr Val
1               5                   10                  15

Ser Asp Cys

<210> SEQ ID NO 10
<211> LENGTH: 26
<212> TYPE: PRT
<213> ORGANISM: Homo sapiens

<400> SEQUENCE: 10

Met Arg Ser Leu Cys Cys Ala Pro Leu Leu Leu Leu Leu Leu Leu Pro
1               5                   10                  15

Leu Leu Leu Thr Pro Pro Ala Gly Asp Ala
            20                  25

<210> SEQ ID NO 11
<211> LENGTH: 96
<212> TYPE: PRT
<213> ORGANISM: Bombina variegata
```

```
<400> SEQUENCE: 11

Met Lys Cys Phe Ala Gln Ile Val Val Leu Leu Val Ile Ala Phe
1               5                  10                 15

Ser His Gly Ala Val Ile Thr Gly Ala Cys Asp Lys Asp Val Gln Cys
            20                  25                  30

Gly Ser Gly Thr Cys Cys Ala Ala Ser Ala Trp Ser Arg Asn Ile Arg
            35                  40                  45

Phe Cys Ile Pro Leu Gly Asn Ser Gly Glu Asp Cys His Pro Ala Ser
            50                  55                  60

His Lys Val Pro Tyr Asp Gly Lys Arg Leu Ser Ser Leu Cys Pro Cys
65                  70                  75                  80

Lys Ser Gly Leu Thr Cys Ser Lys Ser Gly Glu Lys Phe Lys Cys Ser
            85                  90                  95

<210> SEQ ID NO 12
<211> LENGTH: 81
<212> TYPE: PRT
<213> ORGANISM: Dendroaspis polylepis polylepis

<400> SEQUENCE: 12

Ala Val Ile Thr Gly Ala Cys Glu Arg Asp Leu Gln Cys Gly Lys Gly
1               5                  10                 15

Thr Cys Cys Ala Val Ser Leu Trp Ile Lys Ser Val Arg Val Cys Thr
            20                  25                  30

Pro Val Gly Thr Ser Gly Glu Asp Cys His Pro Ala Ser His Lys Ile
            35                  40                  45

Pro Phe Ser Gly Gln Arg Lys Met His His Thr Cys Pro Cys Ala Pro
            50                  55                  60

Asn Leu Ala Cys Val Gln Thr Ser Pro Lys Lys Phe Lys Cys Leu Ser
65                  70                  75                  80

Lys

<210> SEQ ID NO 13
<211> LENGTH: 81
<212> TYPE: PRT
<213> ORGANISM: Artificial Sequence
<220> FEATURE:
<223> OTHER INFORMATION: synthetic construct

<400> SEQUENCE: 13

Ala Val Ile Thr Gly Ala Cys Glu Arg Asp Val Gln Cys Gly Ala Gly
1               5                  10                 15

Thr Cys Cys Ala Ile Ser Leu Trp Leu Arg Gly Leu Arg Met Cys Thr
            20                  25                  30

Pro Leu Gly Arg Glu Gly Glu Glu Cys His Pro Gly Ser His Lys Val
            35                  40                  45

Pro Phe Phe Gly Arg Arg Met His His Thr Cys Pro Cys Leu Pro Gly
            50                  55                  60

Leu Ala Cys Leu Arg Thr Ser Phe Asn Arg Phe Ile Cys Leu Ala Gln
65                  70                  75                  80

Lys

<210> SEQ ID NO 14
<211> LENGTH: 86
<212> TYPE: PRT
<213> ORGANISM: Artificial Sequence
<220> FEATURE:
```

-continued

<223> OTHER INFORMATION: synthetic construct

<400> SEQUENCE: 14

Ala Val Ile Thr Gly Ala Cys Asp Lys Asp Ser Gln Cys Gly Gly Gly
1               5                   10                  15

Met Cys Cys Ala Val Ser Ile Trp Val Lys Ser Ile Arg Ile Cys Thr
            20                  25                  30

Pro Met Gly Lys Leu Gly Asp Ser Cys His Pro Leu Thr Arg Lys Val
        35                  40                  45

Pro Phe Phe Arg Lys Arg Lys His His Thr Cys Pro Cys Leu Pro Asn
50                  55                  60

Leu Leu Cys Ser Arg Phe Pro Asp Gly Arg Tyr Arg Cys Ser Met Asp
65                  70                  75                  80

Leu Lys Asn Ile Asn Phe
                85

<210> SEQ ID NO 15
<211> LENGTH: 89
<212> TYPE: PRT
<213> ORGANISM: Artificial Sequence
<220> FEATURE:
<223> OTHER INFORMATION: synthetic construct

<400> SEQUENCE: 15

Gly Ile Leu Ala Val Ile Thr Gly Ala Cys Glu Arg Asp Val Gln Cys
1               5                   10                  15

Gly Ala Gly Thr Cys Cys Ala Ile Ser Leu Trp Leu Arg Gly Leu Arg
            20                  25                  30

Met Cys Thr Pro Leu Gly Arg Glu Gly Glu Glu Cys His Pro Gly Ser
        35                  40                  45

His Lys Val Pro Phe Phe Arg Lys Arg Lys His His Thr Cys Pro Cys
    50                  55                  60

Leu Pro Asn Leu Leu Cys Ser Arg Phe Pro Asp Gly Arg Tyr Arg Cys
65                  70                  75                  80

Ser Met Asp Leu Lys Asn Ile Asn Phe
                85

<210> SEQ ID NO 16
<211> LENGTH: 85
<212> TYPE: PRT
<213> ORGANISM: Artificial Sequence
<220> FEATURE:
<223> OTHER INFORMATION: synthetic construct

<400> SEQUENCE: 16

Val Ile Thr Gly Ala Cys Glu Arg Asp Val Gln Cys Gly Ala Gly Thr
1               5                   10                  15

Cys Cys Ala Ile Ser Leu Trp Leu Arg Gly Leu Arg Met Cys Thr Pro
            20                  25                  30

Leu Gly Arg Glu Gly Glu Glu Cys His Pro Gly Ser His Lys Val Pro
        35                  40                  45

Phe Phe Arg Lys Arg Lys His His Thr Cys Pro Cys Leu Pro Asn Leu
50                  55                  60

Leu Cys Ser Arg Phe Pro Asp Gly Arg Tyr Arg Cys Ser Met Asp Leu
65                  70                  75                  80

Lys Asn Ile Asn Phe
                85

```
<210> SEQ ID NO 17
<211> LENGTH: 86
<212> TYPE: PRT
<213> ORGANISM: Artificial Sequence
<220> FEATURE:
<223> OTHER INFORMATION: synthetic construct

<400> SEQUENCE: 17

Ala Ala Ala Ala Ala Ala Cys Glu Arg Asp Val Gln Cys Gly Ala Gly
 1               5                  10                  15

Thr Cys Cys Ala Ile Ser Leu Trp Leu Arg Gly Leu Arg Met Cys Thr
                20                  25                  30

Pro Leu Gly Arg Glu Gly Glu Glu Cys His Pro Gly Ser His Lys Val
            35                  40                  45

Pro Phe Phe Arg Lys Arg Lys His His Thr Cys Pro Cys Leu Pro Asn
        50                  55                  60

Leu Leu Cys Ser Arg Phe Pro Asp Gly Arg Tyr Arg Cys Ser Met Asp
65                  70                  75                  80

Leu Lys Asn Ile Asn Phe
                85

<210> SEQ ID NO 18
<211> LENGTH: 87
<212> TYPE: PRT
<213> ORGANISM: Artificial Sequence
<220> FEATURE:
<223> OTHER INFORMATION: synthetic construct

<400> SEQUENCE: 18

Met Ala Val Ile Thr Gly Ala Cys Glu Arg Asp Val Gln Cys Gly Ala
 1               5                  10                  15

Gly Thr Cys Cys Ala Ile Ser Leu Trp Leu Arg Gly Leu Arg Met Cys
                20                  25                  30

Thr Pro Leu Gly Arg Glu Gly Glu Glu Cys His Pro Gly Ser His Lys
            35                  40                  45

Val Pro Phe Phe Arg Lys Arg Lys His His Thr Cys Pro Cys Leu Pro
        50                  55                  60

Asn Leu Leu Cys Ser Arg Phe Pro Asp Gly Arg Tyr Arg Cys Ser Met
65                  70                  75                  80

Asp Leu Lys Asn Ile Asn Phe
                85

<210> SEQ ID NO 19
<211> LENGTH: 14
<212> TYPE: PRT
<213> ORGANISM: Artificial Sequence
<220> FEATURE:
<223> OTHER INFORMATION: synthetic construct

<400> SEQUENCE: 19

Ala Val Ile Thr Gly Ala Cys Glu Arg Asp Val Gln Cys Gly
 1               5                  10
```